US012629079B2

(12) United States Patent
Silence et al.

(10) Patent No.: US 12,629,079 B2
(45) Date of Patent: May 19, 2026

(54) MOBILE ELECTROENCEPHALOGRAM SYSTEM AND METHODS

(71) Applicant: CENSYN, INC., Lake Forest, CA (US)

(72) Inventors: Trevor Gray Silence, Lake Forest, CA (US); Ayushi Hitesh Patel, Lake Forest, CA (US); Anirudh Poornima Bhushan, Lake Forest, CA (US)

(73) Assignee: CenSyn, Inc., Lake Forest, CA (US)

( * ) Notice: Subject to any disclaimer, the term of this patent is extended or adjusted under 35 U.S.C. 154(b) by 664 days.

(21) Appl. No.: 17/903,565

(22) Filed: Sep. 6, 2022

(65) Prior Publication Data

US 2023/0181088 A1 Jun. 15, 2023

Related U.S. Application Data

(63) Continuation of application No. PCT/US2021/020314, filed on Mar. 1, 2021.

(60) Provisional application No. 63/074,955, filed on Sep. 4, 2020, provisional application No. 62/984,246, filed on Mar. 2, 2020.

(51) Int. Cl.
| | |
|---|---|
| *A61B 5/291* | (2021.01) |
| *A61B 5/00* | (2006.01) |
| *A61B 5/369* | (2021.01) |

(52) U.S. Cl.
CPC ............ *A61B 5/291* (2021.01); *A61B 5/0006* (2013.01); *A61B 5/369* (2021.01); *A61B 5/6843* (2013.01); *A61B 2560/0223* (2013.01); *A61B 2560/0431* (2013.01); *A61B 2562/0219* (2013.01); *A61B 2562/0247* (2013.01)

(58) Field of Classification Search
CPC ......... A61B 5/006; A61B 5/291; A61B 5/369; A61B 5/6814; A61B 5/6843; A61B 2560/0223; A61B 2560/0418; A61B 2560/0431; A61B 2562/0219; A61B 2562/0247
See application file for complete search history.

(56) References Cited

U.S. PATENT DOCUMENTS

| | | | |
|---|---|---|---|
| 8,428,681 B2 | 4/2013 | Wilson et al. | |
| 9,215,978 B2 * | 12/2015 | Knight ................ | A61B 5/7203 |
| 9,814,426 B2 | 11/2017 | Connor | |
| 10,076,279 B2 | 9/2018 | Nahum | |
| 2009/0253976 A1 * | 10/2009 | Harlev ................... | A61B 5/343 |
| | | | 606/41 |
| 2012/0143020 A1 * | 6/2012 | Bordoley ............... | A61B 5/291 |
| | | | 600/383 |
| 2017/0281086 A1 * | 10/2017 | Donaldson ............ | A61B 5/1118 |
| 2018/0153470 A1 * | 6/2018 | Gunasekar ........... | A61B 5/6803 |
| 2018/0263523 A1 * | 9/2018 | Puttilli ................. | A61B 5/0077 |
| 2021/0015393 A1 * | 1/2021 | Jordan ................... | A61B 5/291 |

(Continued)

FOREIGN PATENT DOCUMENTS

| | | |
|---|---|---|
| WO | 2018211429 A1 | 11/2018 |
| WO | 2021178319 A1 | 9/2021 |

OTHER PUBLICATIONS

PCT/US2021/020314 filed Mar. 1, 2021 International Search Report and Written Opinion dated May 25, 2021.

*Primary Examiner* — Tse W Chen
(74) *Attorney, Agent, or Firm* — Rutan & Tucker, LLP

(57) ABSTRACT

Provided are systems and method for obtaining electric signal biosignal readings using a portable device.

42 Claims, 35 Drawing Sheets

(56)  References Cited

U.S. PATENT DOCUMENTS

| | | | |
|---|---|---|---|
| 2021/0030297 A1 | 2/2021 | Kouider et al. | |
| 2024/0023820 A1 * | 1/2024 | English | A61B 5/332 |

\* cited by examiner

SECTION FRONT-FRONT

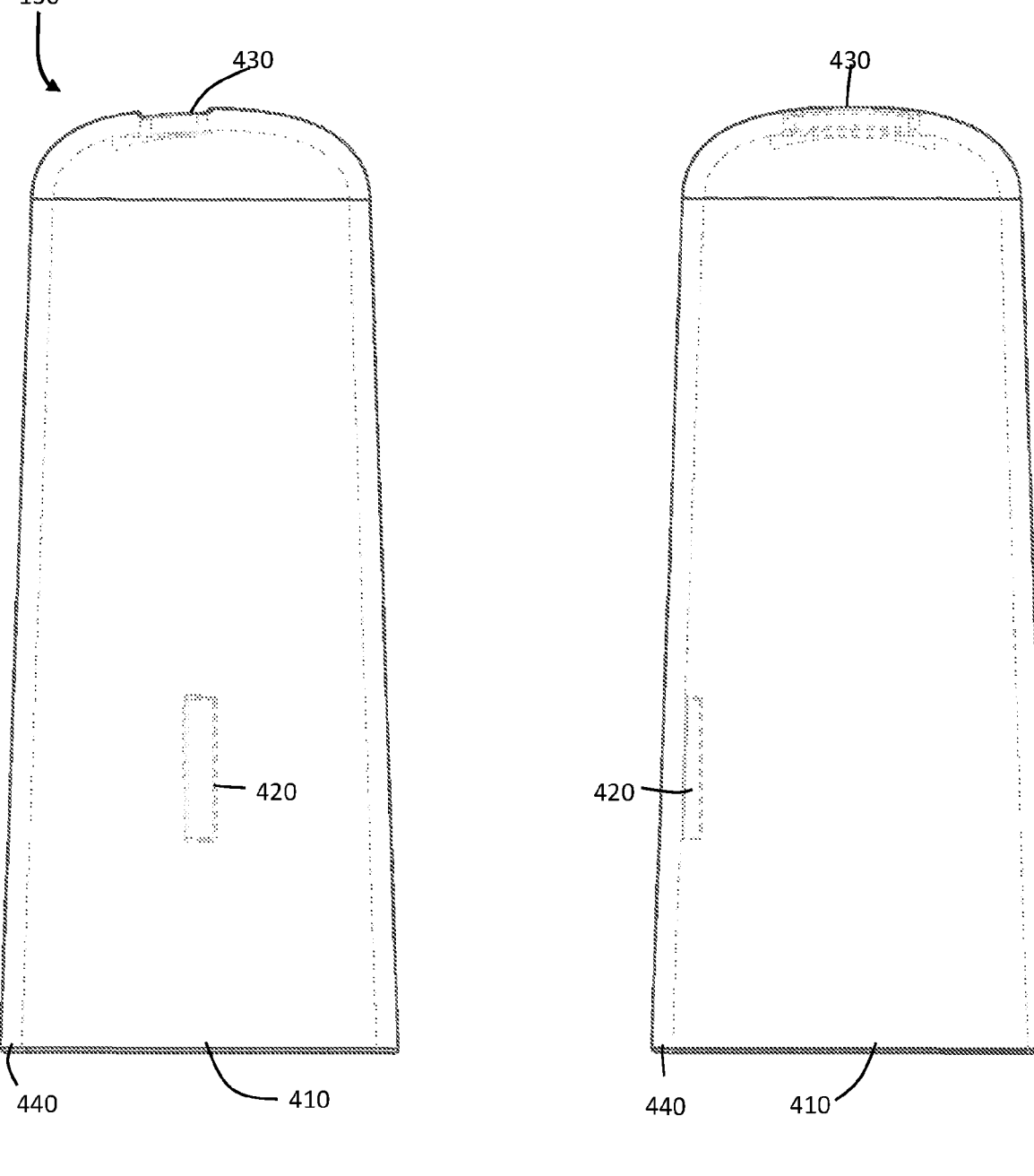
FIG. 4A                                              FIG. 4B

6B

600

130

610

620

630

6B

610

620

630

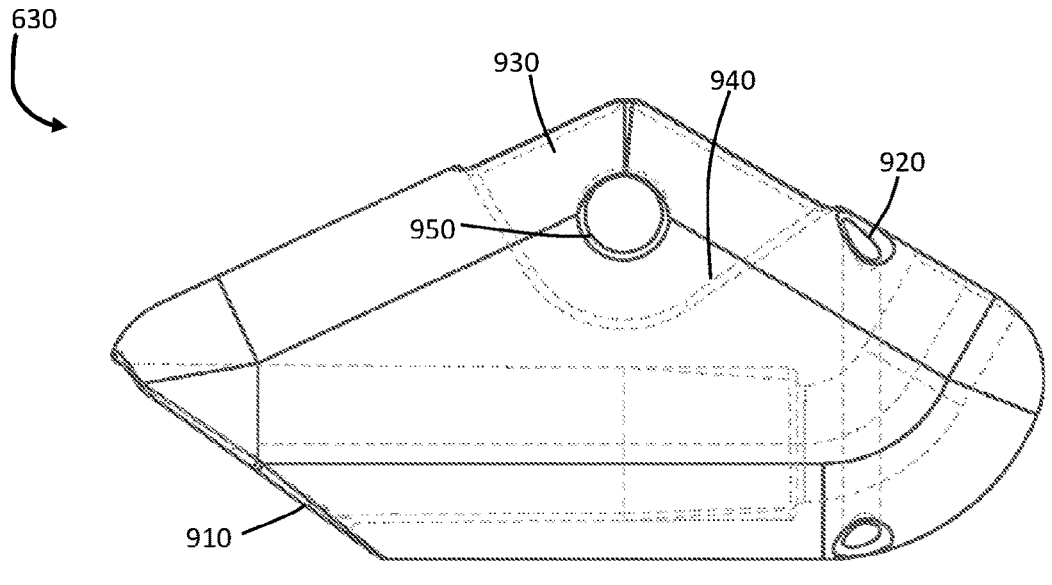
FIG. 9A
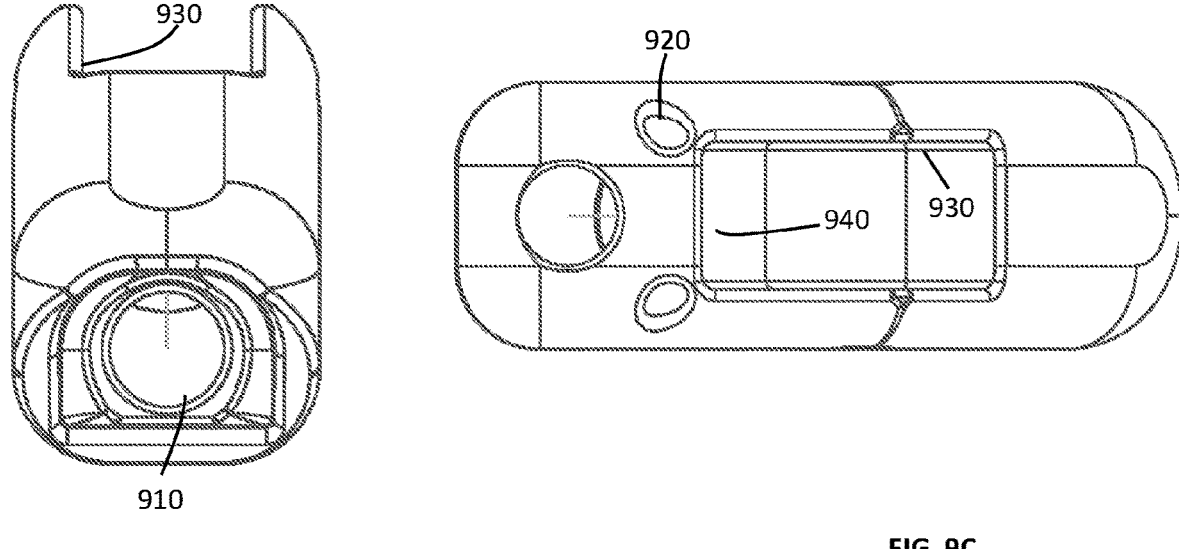
FIG. 9B
FIG. 9C

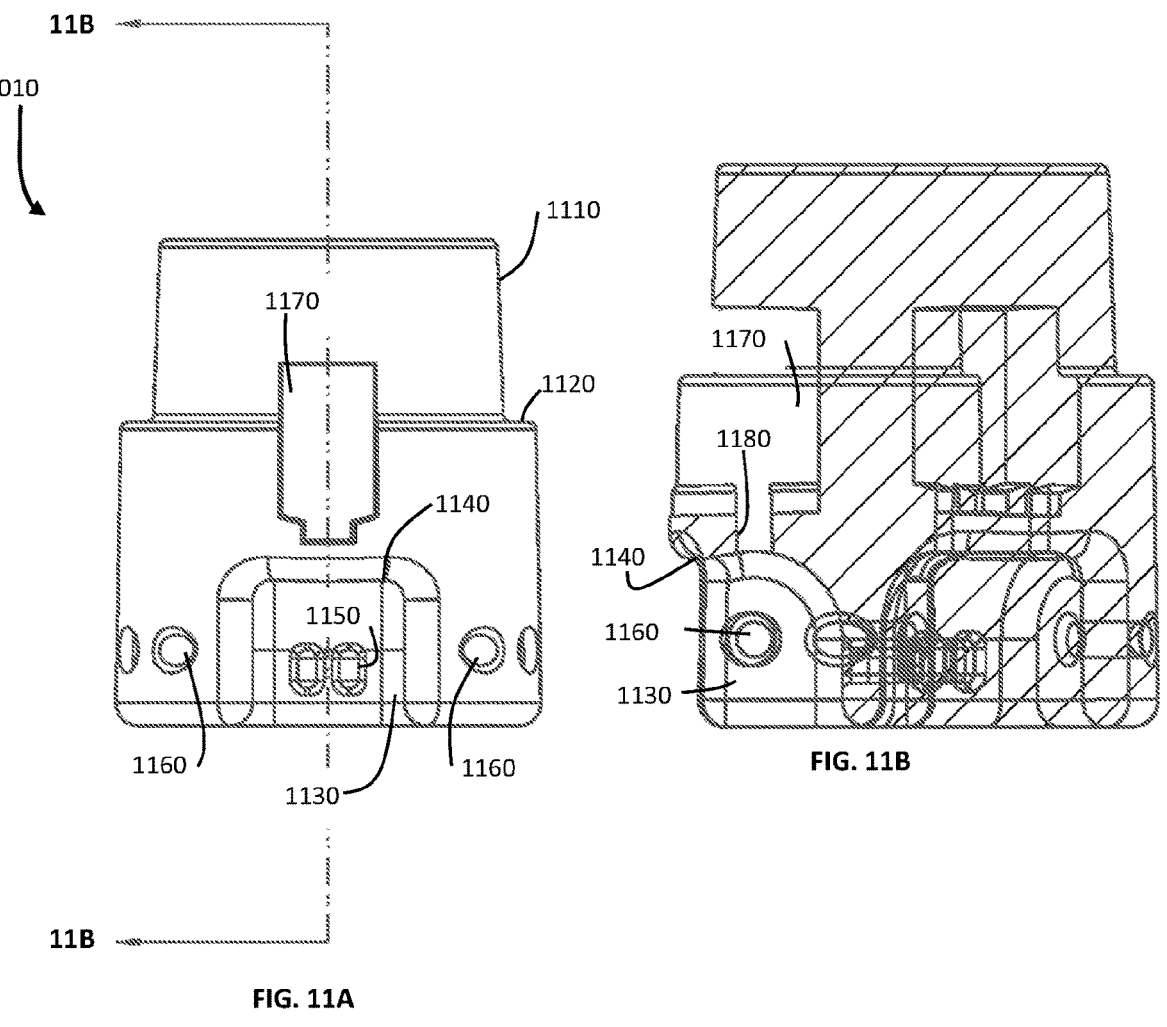
FIG. 11A
FIG. 11B
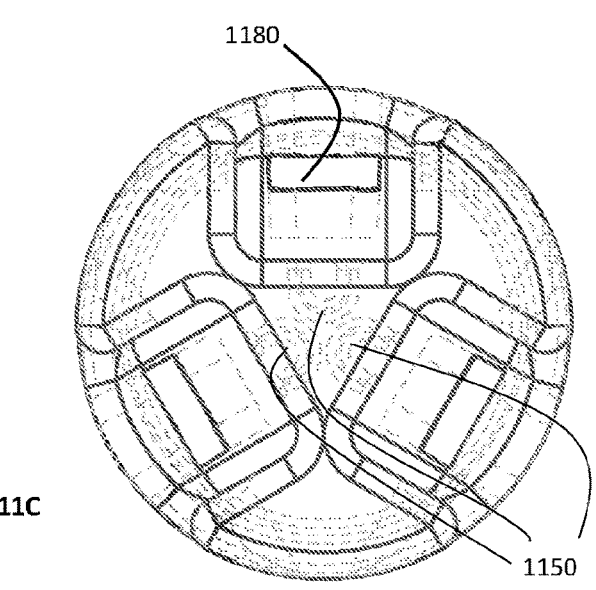
FIG. 11C

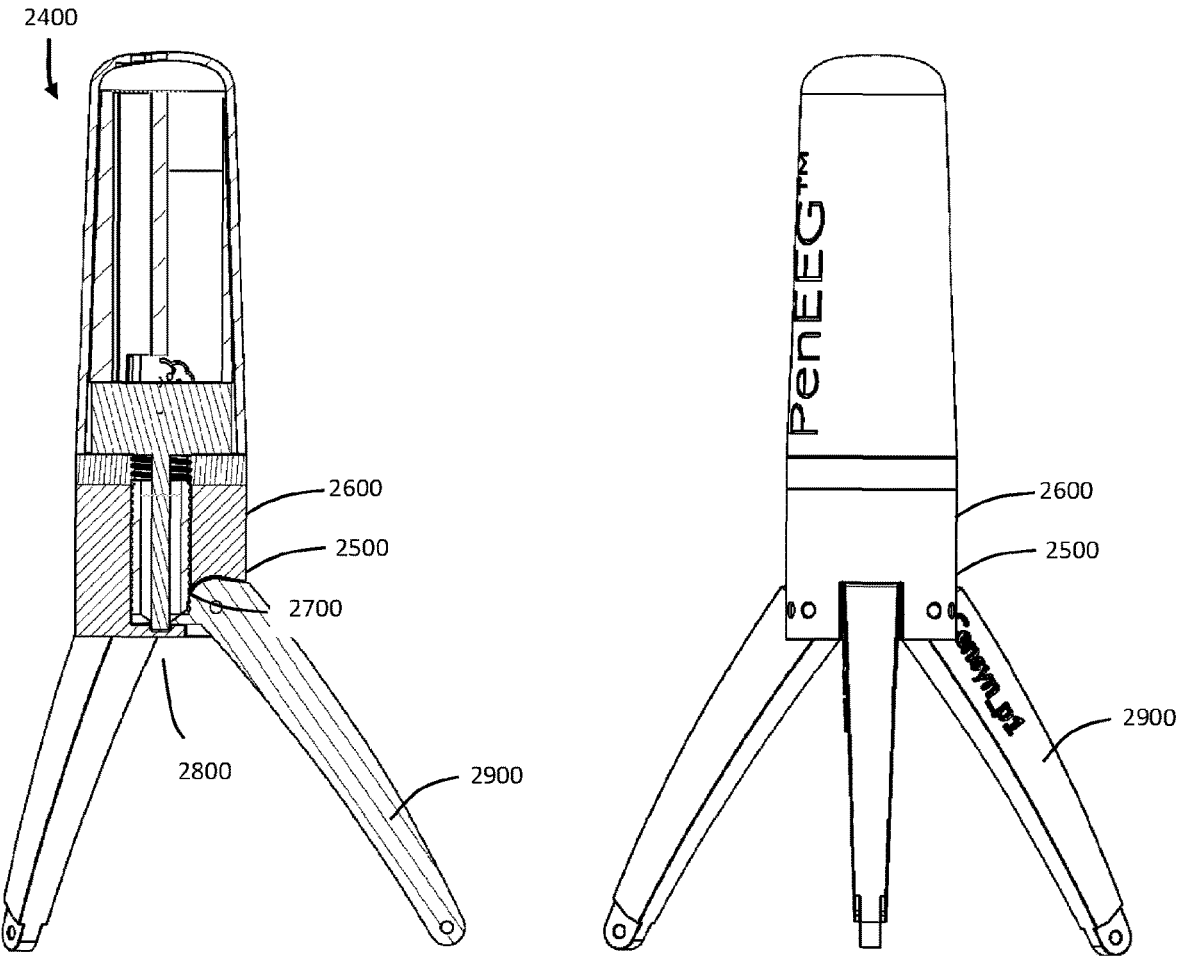
FIG. 24A                    FIG. 24B

2500

2510

2520

2540

2550

2520

2530

2600

2610

2620

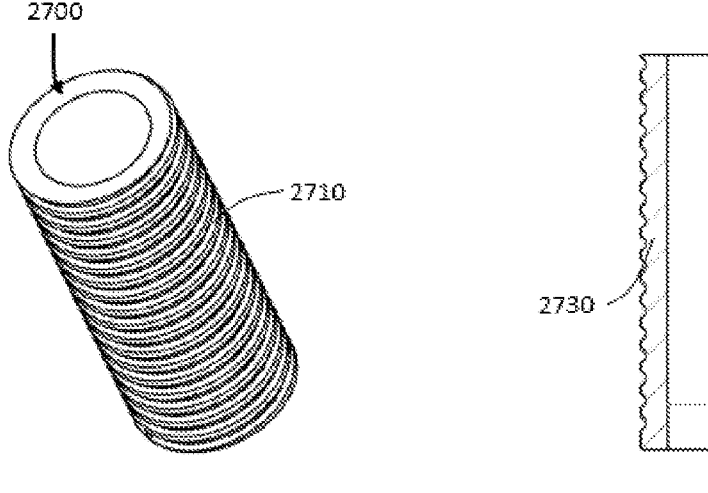
2700
2710
2720
2730
FIG. 27A                    FIG. 27B

3100

3110

3120

3130

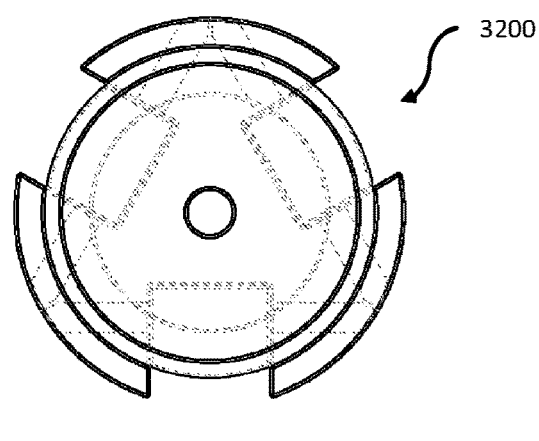
3200
FIG. 32A
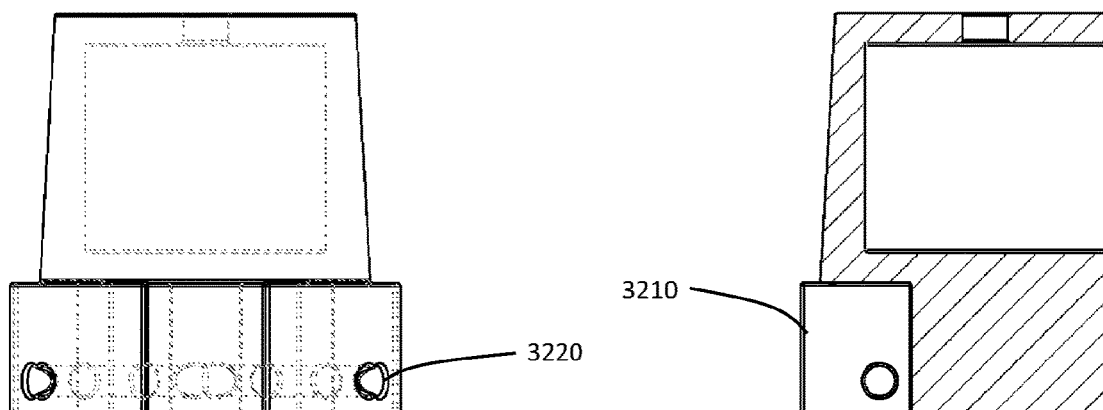
3210
3220
FIG. 32B
FIG. 32C

3600

3650

MOBILE ELECTROENCEPHALOGRAM SYSTEM AND METHODS

CROSS-REFERENCE

This application is a continuation of International Application No. PCT/US2021/020314, filed on 1 Mar. 2021, claims the benefit of U.S. Provisional Application No. 62/984,246, filed Mar. 2, 2020, and further claims benefit of U.S. Provisional Application No. 63/074,955, filed Sep. 4, 2020, which applications are incorporated herein by reference.

BACKGROUND

The electrical signals from a living organism can provide critical diagnostic information. Historically, scientists and physicians have arranged small flat metal discs, called electrodes, on the skin to record bioelectric or electric signals. The electrodes can be configured to record electrocardiogram (ECG) from the heart, electromyogram (EMG) from a muscle group or electroencephalogram (EEG) from the brain. The electrophysiological monitoring method to track and record electrical wave patterns of an organ can provide critical information about its health and functioning.

In particular, most existing technologies use wearable designs that arrange the electrodes using tape, band, straps, caps or headsets to mechanically attach the electrodes on the body part. For either type of application, a substantial amount of time is needed for placement of the electrodes on a patient's scalp by a specialized technician, which prevents the use of EEG to identify brain health in the field such as immediately after an accident for urgent short-term screening or outside of the confines of a hospital or medical center. Rigid geometry designs such as caps or headset system for EEG may not accommodate all head shapes and sizes. Such designs may also inconvenience the medical practitioners as they have to carry multiple devices with different sizes and completely remove the system when there is poor signal quality to exfoliate scalp sites and improve the signal-to-noise ratio.

Current EEG technology is expensive and is complex to setup, requiring a specialized technician for each application of EEG. Several reports in medical literature posit the time criticality of brain dysfunctions. When doctors have to wait up to 48 hours for objective brain data provided by EEGs, they end up treating patients blindly which can cause worse damage to the patient than not treating altogether. In less populated areas, the time from injury to monitoring increases greatly effecting the outcomes of those patients.

Different groups have attempted to create confined wearable systems with a reduced number of electrodes that may reduce the complexity of setup but they present their own limitations. For example, an EEG headband that sits on the crown may lack critical coverage of patient's central scalp region, reducing their versatility to screen different brain conditions. Some wearable designs have utilized an array of electrodes in a fixed pattern worn by the operator on one finger or multiple fingers like a glove. Multiple electrodes on a fabric glove present challenges in manufacturing, fragility and convenience. The loose wires may introduce additional motion artifact to sensitive electric signals. Such operator wearable designs may also increase the chances of cross-infection if there is a tear in the holding fabric. Some handheld EEG devices require professionals in electrode placement for application and have not accounted for subtle motion artifacts from holding the device to the scalp'.

EEG devices that are easy to use and rapidly deploy to multiple configurations with reduced number of electrodes will ensure that doctors would not have to wait for technicians and machines to become available, potentially saving lives and reducing hospital liability in the process. Such devices act as flexible montage systems where a limited number of electrodes can be moved to different configurations to get a wider coverage.

Annually in the United States, a total of 2.5 million patients present nonconvulsive seizures (NCS). Consequently, when NCS persists for more than 5 minutes, the patient enters nonconvulsive status epilepticus (NCSE). NCSE is characterized as prolonged, high-amplitude, uncontrolled electrical disturbances in the brain. It can be only diagnosed using EEGs due to lack of any overt clinical signs and its common presentation alongside altered mental state. Furthermore, NCSE also presents in 23% of all neuro-ICU patients with critical illnesses such as stroke, cardiac arrest and traumatic brain injury. Due to the critical illnesses associated with NCSE, patients suffer from up to 51% mortality, high morbidity and cognitive dysfunction. However, even the most well-established, high-capacity hospitals possess a limited number of machines, with many smaller hospitals lacking any EEG equipment at all. During the night shift, there are less technicians available on-site for setup, leaving even the physicians without immediate access to the EEG needed for NCSE diagnosis.

NCSE is misdiagnosed in up to 93% cases in the emergency departments due to subjective assessments and several cases are unaccounted for due to under-diagnosis. Current clinical guidelines and time sensitivity of these seizures compels neurologists to administer anti-epileptic drugs (AED) based on clinical impressions rather than waiting for EEG data. However, uninformed treatment without EEG can result in a similar mortality rate as NCSE left untreated. Several AEDs, such as benzodiazepines, cause significant hypotension and respiratory suppression in up to 40% of patients. Patients suffering from respiratory suppression require intubation and are admitted to the intensive care unit (ICU). Evidence from studies show that 10-15% of patients were treated with AED's suspected based on clinical impressions only but were later found to have normal EEG activity. Thus, an easy to setup flexible montage EEG will increase the frequency of EEG evaluation during rounds and at initial suspicion, increasing the administration of accurate treatments.

Portable and flexible montage EEGs may also create a gateway for objective concussion or mild traumatic brain injury screening. There are over 5.5 million suspected concussion cases each year with athletes in high impact sports disproportionately affected. Current concussion screening protocols are unreliable and miss half of all cases for mild injuries. Subjective questionnaires like the Sport Concussion Assessment Tool-3 are vulnerable to tester bias and lack a long-term perspective of patient recovery. Imaging techniques like computed tomography are done at the hospital and miss 91% of concussion cases. Easy-to-use and self-administrable flexible montage EEGs can dramatically simplify the data collection process when compared to existing technologies. Now, athletes can record a healthy baseline EEG when they are injury-free. Coaches and trainers can administer such devices on the sidelines to record EEGs right after an injury and the athlete can self-administer it from their home to monitor recovery. With this simplified process, we can track athlete health all the way from high school through the end of their professional career. This is critical as detrimental effects of concussions are often caused by cumulative mild trauma.

SUMMARY

Provided herein are embodiments of portable system for receiving electric signals from a surface, comprising: a portable device for detecting electrical activity comprising: a housing; one or more legs extending from the housing; one or more electrodes provided on a distal end of each of the one or more legs; one or more sensors configured to determine a position of the one or more electrodes, wherein the one or more electrodes are placed on the surface to detect the electric signals.

In some embodiments, the system further comprises a first computing device provided within the housing, the first computing device comprising a processor operatively coupled to the one or more sensor and a non-transitory computer readable storage medium with a computer program including instructions executable by the processor causing the processor to: i) calibrate a position of the one or more electrodes and set an origin, ii) receive data from the one or more sensors to track the position of the one or more electrodes, and iii) record the electric signals detected by the one or more electrodes.

In some embodiments, the processor of the first computing device is further configured to transmit the electrical signal to a second computing device, the second computing device configured to receive the electric signals transmitted from the first computing device of the portable device and positional data corresponding to the position of the one or more electrodes, and wherein the second computing device comprises a second processor and a non-transitory computer readable storage medium with a second computer program including instructions executable by the processor causing the second processor to generate a graphical representation of the electrical signals detected by the one or more electrodes. In some embodiments, the second computer program further comprises instructions to generate a graphical representation of the positional data of the one or more electrodes. In some embodiments, the first computing device communicates to the second computing device via wireless networking. In some embodiments, the wireless networking comprises Bluetooth transmission.

In some embodiments, the one or more sensors comprise an image sensor. In some embodiments, the image sensor is a camera. In some embodiments, the camera is a 120° field of view camera. In some embodiments, the camera is positioned such that the electrodes are within a field of view of the camera.

In some embodiments, the portable device further comprises one or more inertial sensors, and wherein the computer program includes further instructions causing the processor to receive data from the one or more inertial sensors to track the position of the one or more electrodes. In some embodiments, the one or more inertial sensors are configured to provide a six-axis information by combining accelerometer and gyroscope. In some embodiments, the housing further comprises a port to reversibly receive a wired electrode.

The system of any one of claim 1, wherein the portable device further comprises one or more feet, each foot provided at a distal end of the one or more legs, wherein the one or more electrodes are disposed on the one or more feet. In some embodiments, each foot comprises a compressible pad. In some embodiments, each foot is connected to each leg via a pin joint. In some embodiments, the portable device further comprises one or more tension wires, each tension wire running from a foot of the one or more feet, through a leg connected to said foot, and to the housing.

In some embodiments, the portable device further comprises one or more force sensors, wherein the force sensors measure a force applied to the surface by the one or more electrodes. In some embodiments, one force sensor is provided for each of the one or more legs. In some embodiments, the portable device further comprises one or more force sensors, wherein the force sensors measure a force applied to the surface of the subject by the one or more electrodes. In some embodiments, the one or more electrodes comprise gold-cup electrodes. In some embodiments, the portable device further comprises a battery.

In some embodiments, the portable device comprises a closed configuration and an open configuration, wherein the one or more electrodes are closer to one another in the closed configuration than in the open configuration. In some embodiments, the portable device further comprises one or more tension wires, each tension wire running from the distal end of each leg, through each leg, and to the housing. In some embodiments, the tension wire biases the one or more legs to the closed configuration. In some embodiments, the housing comprises openings sized to fit the one or more legs to limit a distance between the one or more electrodes in the open configuration.

In some embodiments, the portable device comprises three legs. In some embodiments, the portable device further comprises one or more feet, each foot provided at a distal end of the one or more legs, wherein the one or more electrodes are disposed on the one or more feet. In some embodiments, each foot comprises a compressible pad. In some embodiments, each foot is connected to each leg via a pin joint. In some embodiments, the portable device further comprises one or more tension wires, each tension wire running from a foot of the one or more feet, through a leg connected to said foot, and to the housing. In some embodiments, the portable device comprises a closed configuration and an open configuration, wherein the one or more electrodes are closer to one another in the closed configuration than in the open configuration, and wherein the tension wire biases the one or more legs to the closed configuration.

In some embodiments, the portable device comprises an actuator to rotate the one or more legs. In some embodiments, rotation of the one or more legs comprises a rotation toward or away from a center axis of the portable device such that the electrodes move toward or away from one another. In some embodiments, the actuator rotates the one or more legs simultaneously.

In some embodiments, the one or more tension wires are configured to keep the one or more electrodes in contact with the surface while taking receiving the electric signals. In some embodiments, the surface is a skin surface of a subject. In some embodiments, the skin surface is a scalp of a subject, and the system is configured to generate an electroencephalogram.

Provided herein are embodiments of a method for detecting electric signals from a with a portable device, the portable device comprising: a housing; one or more legs extending from the housing; one or more electrodes provided on a distal end of each of the one or more legs; and one or more sensors configured to determine a position of the one or more electrodes, the method comprising: placing the one or more electrodes on a surface of a subject to detect one or more electric signals from a first region of the surface of the subject; moving the one or more electrodes to a subsequent region of the surface of the subject; detecting one or more electric signals from the subsequent region of the surface of the subject; repeating steps (b) and (c) until one or more electric signals have been obtained from all desired regions of the surface of the subject.

In some embodiments, the step of moving the one or more electrodes to the subsequent region of the surface of the subject further comprises keeping the one or more electrodes in contact with the surface of the subject. In some embodiments, the method further comprises a step of holding the one or more electrodes at the first region and a step of holding the one or more electrodes at the subsequent region. In some embodiments, the method further comprises a step of receiving feedback from the portable device prior to moving the one or more electrodes to the subsequent region. In some embodiments, the feedback is indicative of the transmitting of the electrical signals obtained by the one or more electrodes. In some embodiments, the feedback is indicative of the capturing and storing of data corresponding to the electrical signals obtained by the one or more electrodes. In some embodiments, the data comprises a position of each of the one or more electrodes. In some embodiments, the data comprises voltage fluctuations detected by the one or more electrodes. In some embodiments, the feedback comprises haptic feedback, visual feedback, or a combination thereof.

In some embodiments, the surface of the subject is a scalp. In some embodiments, the method generates an electroencephalogram, and wherein the portable device in configured as a portable electroencephalogram device. In some embodiments, the method is performed by the subject. In some embodiments, the method further comprises a step of engaging a button on the portable device to calibrate the position of the one or more electrodes at the origin.

In some embodiments, the portable device further comprises a computing device provided within the housing, the computing device comprising a processor operatively coupled to the image sensor and a non-transitory computer readable storage medium with a computer program including instructions executable by the processor causing the processor to: i) calibrate a position of the one or more electrodes and set an origin, ii) receive data from the one or more sensors to track the position of the one or more electrodes, and iii) record electric signals obtained from the one or more electrodes. In some embodiments, the processor of the computing device is further configured to transmit the electrical signals to an external computing device.

In some embodiments, provided herein is a portable system for receiving electric signals from a surface, comprising: a portable device for detecting electrical activity comprising: a housing; one or more legs extending from the housing; one or more electrodes provided on a distal end of each of the one or more legs; and one or more sensors configured to determine a position of the one or more electrodes, wherein the one or more electrodes are placed on the surface to detect the electric signals.

In some embodiments, provided herein is a portable system for receiving electric signals from a surface, comprising: a portable device for detecting electrical activity comprising: a housing; one or more legs extending from the housing; one or more electrodes provided on a distal end of each of the one or more legs; and one or more sensors configured to determine a position of the one or more electrodes, wherein the one or more electrodes are placed on the surface to detect the electric signals; and a first computing device provided within the housing, the first computing device comprising a processor operatively coupled to the one or more sensor and a non-transitory computer readable storage medium with a computer program including instructions executable by the processor causing the processor to: calibrate a position of the one or more electrodes and set an origin, receive data from the one or more sensors to track the position of the one or more electrodes, and record the electric signals detected by the one or more electrodes.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4A illustrates a body of the biosignal acquisition device of FIG. 1A, according to some embodiments.

FIG. 4B illustrates a side view of the body of a biosignal acquisition device showing a supporting structure, according to some embodiments.

FIG. 9A illustrates a foot of the housing of the biosignal acquisition device of FIG. 7A, according to some embodiments.

FIG. 9B illustrates an opening sized to retain a conventional EEG electrode and wires routed through a channel of a leg of the EEG device, according to some embodiments.

FIG. 9C illustrates a top view of the foot showing securing point, constraining surface and cut, according to some embodiments.

FIG. 11A illustrates a housing of the biosignal acquisition device of FIG. 10A, according to some embodiments FIG. 11B is a cross-sectional view of the housing depicted in FIG. 11A along line 11B-11B showing a constraining surface and a cut, according to some embodiments.

FIG. 11C is bottom view of the housing showing a supporting structure and a cut, according to some embodiments.

FIG. 24A illustrates a cross section view of exemplary embodiment of a housing encompassing a thumb-driven rotary gear mechanism to interface with a leg to rotate to a position, according to some embodiments.

FIG. 24B illustrates a front view of exemplary embodiment of a housing encompassing a thumb-driven rotary gear mechanism to interface with a leg to rotate to a position, according to some embodiments.

FIG. 27A illustrates an isometric view of translator including outer threads, according to some embodiments.

FIG. 27B illustrates a cross section view of translator highlighting inner cut and surface, according to some embodiments.

FIG. 32A illustrates a top down view of housing showing the trimetric distribution of features, according to some embodiments.

FIG. 32B illustrates a front view of housing including a cut for leg and holes for axis rotation, according to some embodiments.

FIG. 32C illustrates a cross section view of housing showing a cut for leg and hole, according to some embodiments.

DETAILED DESCRIPTION

Figures 1A, 1B:
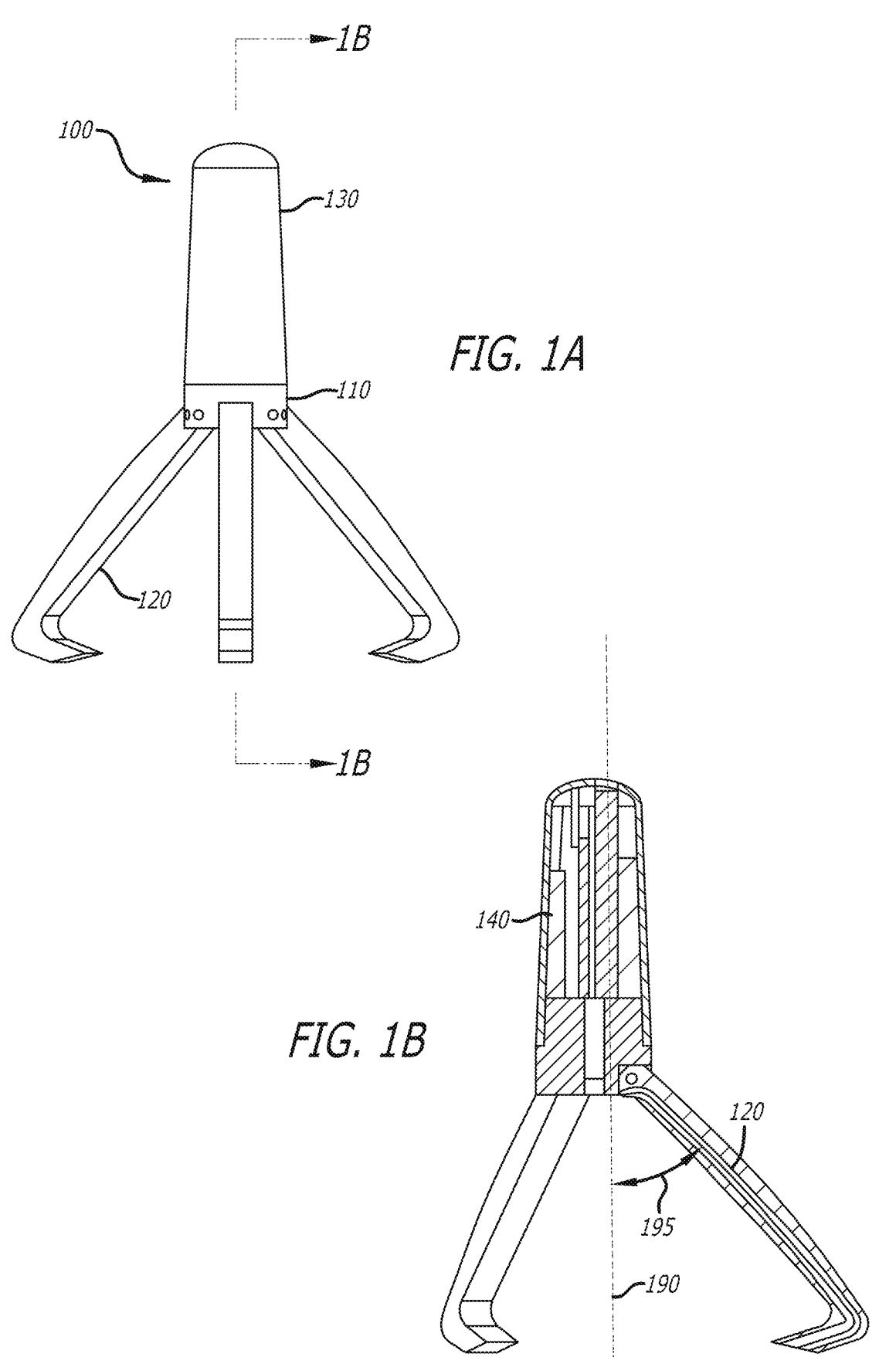
FIG. 1A depicts a biosignal acquisition device operating as a flexible montage brain monitoring system, according to some embodiments.
FIG. 1B illustrates a cross-sectional view of a biosignal acquisition device of FIG. 1A along a cross-sectional line 1B-1B, according to some embodiments.

Embodiments disclosed relate to an architecture for a portable device for measuring electrical signals from a surface. In some embodiments, the surface is a skin surface of a subject. In some embodiments, the surface of the subject is a scalp and the portable device is configured as an electroencephalogram (EEG) device. In some embodiments, the portable EEG device is configured with greater electrode adjustability that enables greater ease of use than possible with traditional taped or head-wearable based EEG currently available on the market. This will allow for easier access to targeted areas of the brain leading to an overall decrease in time to monitor patient brain data. The configuration may further allow for self-administration of testing and/or monitoring, such as electroencephalography or electrophysiological monitoring. The configuration may allow for someone who is inexperienced in electroencephalography to obtain accurate electroencephalogram readings to provide sufficient data for monitoring of brain activity and/or diagnosis of health conditions.

In some embodiments, provided herein is a PenEEG (pEEG) device. In some embodiments, PenEEG is a handheld, configurable electrode, two-channel system that provides expedited NCSE identification with minimal training to operate. As such the pEEG may be rapidly deployed for NCSE screening in one-minute. In some embodiments, when a clinician suspects NCSE, they will 1) retrieve the device, 2) activate a tablet application which pairs with the pEEG, and 3) apply the pEEG to the first screening location on a patient's scalp. Nurses and technicians may also operate the device if the clinician is off-site. The tablet may indicate the first screening configuration to the operator, prompting them to then exfoliate those locations. The three pivoting legs of the pEEG may be opened. The legs of the device may comprise cup electrodes at the distal end. The electrodes may be prepared by the application of the conductive gel. In some embodiments, the pEEG is placed on the scalp and an image-based tracking system verifies that the actual position matches the position indicated for each electrode in a configuration. In some embodiments, an integrated smart feedback system in the pEEG tracks the electrode contact and alerts the operator when the contact is insufficient and requires adjustments. EEG signals may be displayed on the tablet in real-time as the operator records thirty-second epochs at each indicated configuration to acquire sufficient data for seizure activity quantification. This may allow clinicians to make informed, expedited treatment decisions during on-site or off-site review.

Ease of use may position the pEEG system for rapid adoption by neurologists, nurses, and EEG technicians alike for on-the-go monitoring. The configurable electrode system may be analogous to a stethoscope with 2 channels, designed to be rapidly repositioned at multiple electrode configurations on the scalp.

A guided electrode positioning system (GePS) is designed to minimize the actions taken by an operator during use. The GePS tracks the device position to A) verify if the operator has precisely aligned the electrodes at the correct configuration and B) automatically catalog the EEG signal with the verified configuration. Automated tracking and cataloging through GePS reduces the operational workload of data management and expedites data access for future review.

According to some embodiments of the disclosure, the EEG device features a housing to provide a central body by which links and electrodes can be adjusted, wherein a plurality of electrode positions and angles can be achieved. The position of the electrode is adjustable, as one or more segments forming the leg can be angled in relation to the housing to change the angle of attack by the electrode when placing on the scalp. As a result, a single portable EEG device may be compatible for any montage accessible via traditional EEG. The adjustability and ability to rapidly position this EEG at multiple montages over a couple minutes will combat the disadvantages associated with the setup and administration of the traditional and head-mounted EEG systems, allowing for easier access to brain data and decreased procedural times resulting in better treatment for patients.

Some embodiments of this improved EEG and housing includes two main components: a housing and one or more legs (hereinafter, "leg"). The leg of may be fixed in the open position using physical barriers such as interior surfaces sized to fit exterior surfaces of the leg. In this way, the leg cannot be rotated about the pin axis of the housing and provide a sturdy design for single positional reading. The legs may be rigid or semi-rigid such that a force supplied by the user can be translated through the legs to facilitate proper contact of the electrodes to the skin surface.

An electrode with adjustable positioning can decrease the time it takes to set up and record brain signals, allowing for rapid switching between montages to provide a glance at brain function at critical areas across the brain. Neurologists, nurses, paramedics, EEG technicians can quickly read areas that would usually require a lengthy setup and preparation process. This device can also be self-administered for personal screening at home or on the go. Furthermore, an adjustable electrode allows for adaptive positioning based on each patient's head size, providing the same one-size-fits-all functionality as present in taped electrodes to portable, wireless EEG.

Lastly, another advantage of the resulting electrode adjustability is overall improved triage of patients. When using the quick and portable EEG to perform a quick reading, the full EEG can be directed to patients who need it most; if the quick EEG spots problematic brain patterns, then a full EEG can be called. If nothing apparently dysfunctional is spotted upon initial reading with the adjustable electrode EEG, then the patient may be at a lower priority for the full EEG reading. While the system described herein does offer discrete EEG monitoring, wired electrodes can be connected to the same to provide continuous monitoring at one montage.

Referring to FIG. 1A, an EEG device 100 operating as a flexible montage brain monitoring system is shown, according to some embodiments. In some embodiments, the EEG device 100 features a plurality of components, including a housing 110, legs 120, and body 130. A portion of the housing 110 may be inserted through an opening of the body 130, while portions of each of the legs 120 are inserted into openings in the housing 110. Apertures in the housing 110 and legs 120 may each be sized to fit a pin to secure that leg 120 in a housing 110 opening. Alternatively, one or more of these legs 120 may be secured using adhesive or a fusing process. An opening in the body 130 may be threaded or secured to the housing 110 using adhesive or a fusing process.

As illustrated in FIG. 1B, a cross-sectional view of the EEG device 100 of FIG. 1A along line 1B-1B is shown. In some embodiments, the housing 110 may be entered into the body 130 opening. The body 130 may be sized to fit electrical components necessary to record signals and provide portability which sit above the housing 110. The housing 110 openings may be sized to fit the leg 130 extrusions incorporate a feature design to prevent rotation of the leg 130. This feature paired with a similar feature on the legs 130 keep the legs 130 in an open position may allow for quick relocation of electrodes to accommodate multiple montages with minimal adjustment.

Figures 2A, 2B:
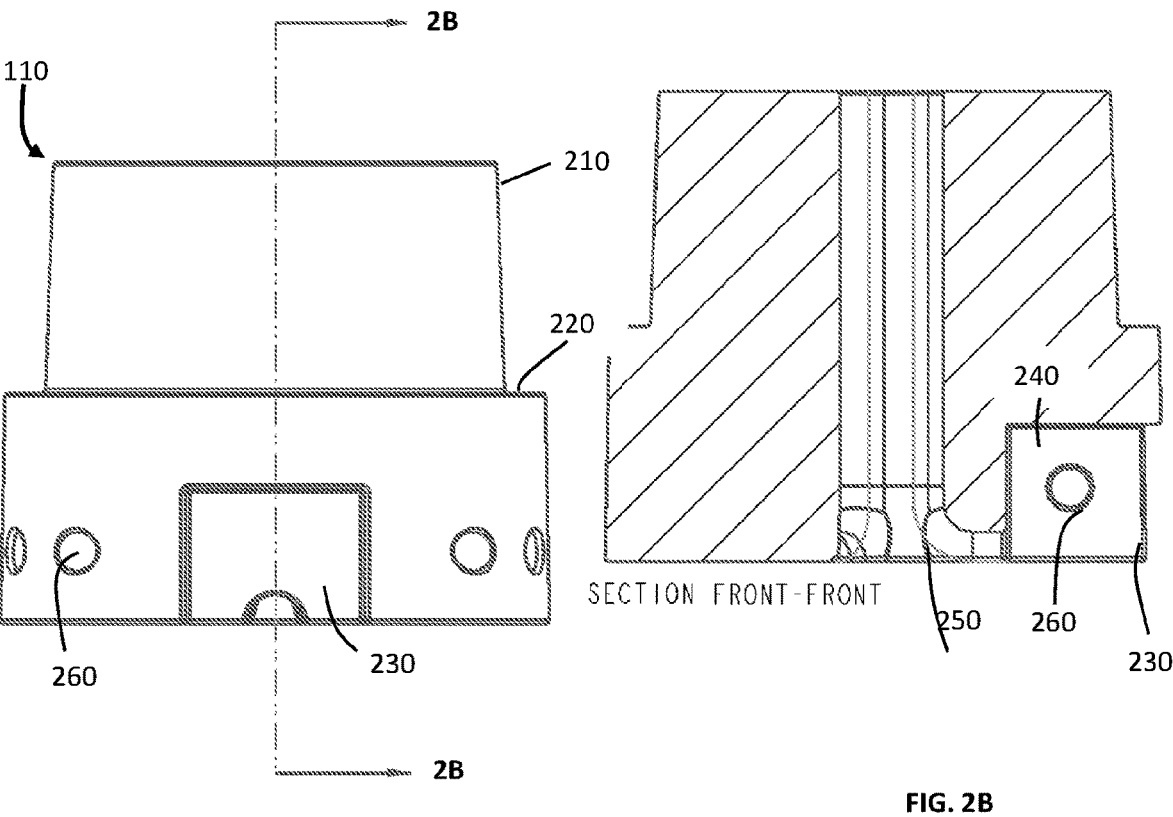
FIG. 2A illustrates a housing of the biosignal acquisition device of FIG. 1A, according to some embodiments.
FIG. 2B illustrates a cross-sectional view of the housing depicted in FIG. 2A along line 2B-2B, according to some embodiments.

Referring now to FIGS. 2A and 2B, the housing 110 is shown, according to some embodiments. In some embodiments, the housing 110 includes an extrusion 210, a constraining surface 220, an opening 230, a second constraining surface 240, a cut 250, and one or more securing points 260. The extrusion 210 may be sized to fit the opening on the body 130 while the constraining surface 220 serves to limit the entry of housing 110 into the body 130. The opening 230 may be sized to fit an extrusion on the leg 120 while the second constraining surface 240 fits with an angled surface (310 as depicted in FIGS. 3A-3B) on the leg 120 to prevent movement or rotation when the leg 120 is fixed to the securing point 260, keeping the leg 120 in an open position.

As shown in FIG. 2B, the opening 230, the second constraining surface 240, the cut 250, and at securing point 260 are made apparent. A cut 250 through the housing 110 may provide a route for electrode wire starting from the distal end of the leg 120 to reach the electrical components contained in the body 130. As shown in FIG. 2B, the opening 230, the second constraining surface 240, the cut 250, and at securing point 260 are made apparent. The angled feature of the constraining surface 240 may prevent rotation about the securing point 260.

Figure 3A:
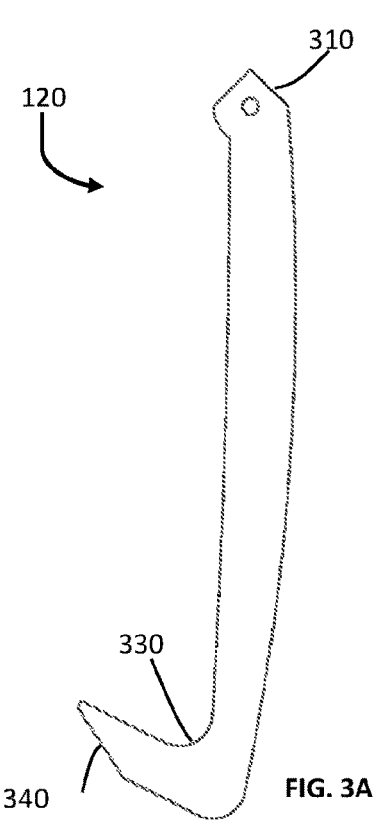
FIG. 3A depicts a leg of the biosignal acquisition device of FIG. 1A, according to some embodiments.
Figure 3B:
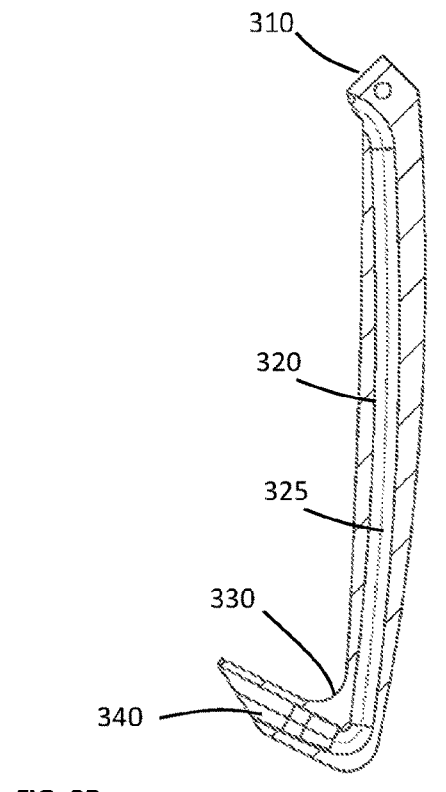
FIG. 3B illustrates a cross-sectional view of the leg depicted in FIG. 3C along line 3B-3B, according to some embodiments.
Figure 3C:
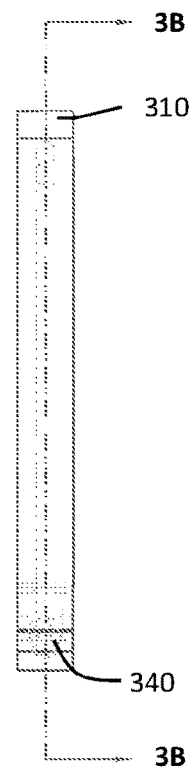
FIG. 3C illustrates a front view of a leg of FIG. 3A, according to some embodiments.

Referring now to FIGS. 3A and 3B, the leg 120 is shown, according to some embodiments. In some embodiments, the leg 120 may include an angled extrusion 310, a channel 320, a bend 330, and an opening 340. An angled extrusion 310 may be sized to fit the opening 230 and constraining surface 240 of the housing 110. When the leg 120 is attached to the housing 110 via the securing point 260, these features may prevent movement of the leg 120, allowing for rapid switching of positions to different montages across the scalp with minimal adjustment needed. Since the legs 120 of this embodiment are secured in an open position, a bend 330 may be required to maintain contact between electrode and patient scalp. As shown in FIG. 3B, an opening 340 may be sized to fit electrodes traditionally used with EEG machines. The electrode wire 325 may then travel up the channel 320 and through the cut 250 of the housing 110 to provide a signal to the electrical components in the body 130. In some embodiments, the wall of the channel 320 is shielded to protect the electrode wire from radiative noise. In some embodiments, the channel 320 provides a path for both the electrode wire and a tendon.

As depicted in FIG. 1B, a constraining surface (e.g. 240) may limit rotation of the legs 120 with respect to the center axis 190 of the housing 130. In some embodiments, a constraining surface limits the angle 195 formed between the leg 120 and the center axis 190 to about 45° in an open configuration. In some embodiments, the angle between the leg and the center axis in the open configuration is limited to about 35° to about 65°. In some embodiments, the angle between the leg and the center axis in the open configuration is limited to about 35° to about 40°, about 35° to about 45°, about 35° to about 50°, about 35° to about 55°, about 35° to about 60°, about 35° to about 65°, about 40° to about 45°, about 40° to about 50°, about 40° to about 55°, about 40° to about 60°, about 40° to about 65°, about 45° to about 50°, about 45° to about 55°, about 45° to about 60°, about 45° to about 65°, about 50° to about 55°, about 50° to about 60°, about 50° to about 65°, about 55° to about 60°, about 55° to about 65°, or about 60° to about 65°. In some embodiments, the angle between the leg and the center axis in the open configuration is limited to about 35°, about 40°, about 45°, about 50°, about 55°, about 60°, or about 65°. In some embodiments, the angle between the leg and the center axis in the open configuration is limited to at least about 35°, about 40°, about 45°, about 50°, about 55°, or about 60°. In some embodiments, the angle between the leg and the center axis in the open configuration is limited to at most about 40°, about 45°, about 50°, about 55°, about 60°, or about 65°. Multiple embodiments of constraining surfaces (e.g. 240, 740, 1140, etc.) which contact angled surfaces (e.g. 310, 850, 1250, etc.) to restrict movement of the leg and limit the angle between the leg and the center axis of the housing are depicted in the accompanying figures and described herein.

Figures 5A, 5B, 5C:
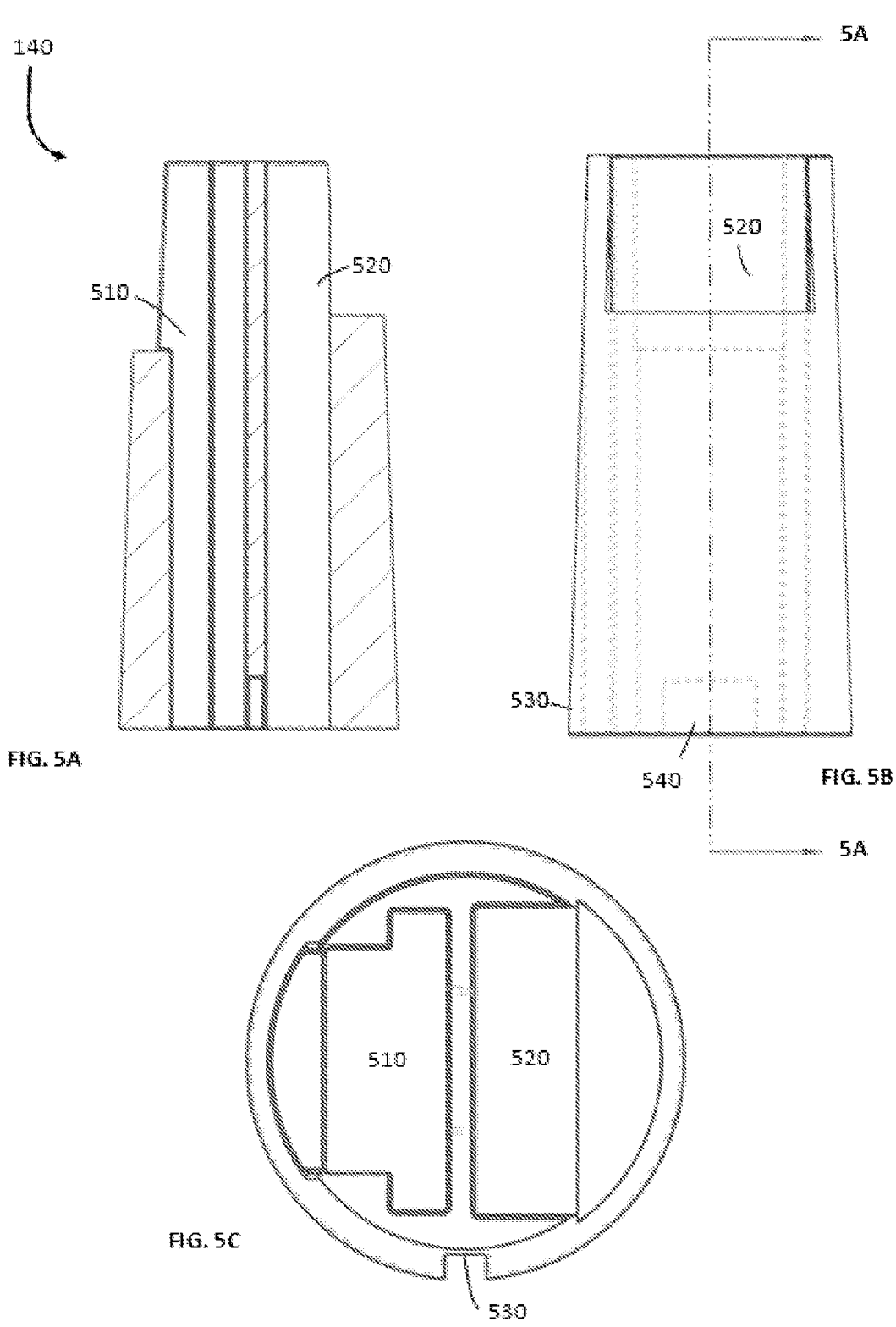
FIG. 5A shows a cross section view a package 140 of the biosignal acquisition device of FIG. 5B taken along line 5A-5A and illustrates an opening made allowing wires to pass between a first slot and a second slot of the package, according to some embodiments.
FIG. 5B. illustrates a package 140 of the biosignal acquisition device of FIG. 1A, according to some embodiments.
FIG. 5C illustrates a positioning structure that residing within the body depicted in FIG. 4A positioning structure, according to some embodiments.

Referring now to FIG. 4A, the body 130 is shown, according to some embodiments. In some embodiments, the body 130 includes an opening 410, a positioning structure 420, a port 430 and an edge 440. The opening 410 is sized to fit the extrusion 210 of the housing 110, while the edge 440 contacts the constraining surface 220 of the housing 110 to prevent the body 130 from fully encompassing the housing 110. As shown in FIG. 4B, a positioning structure 420 is sized to fit a positioning structure (530 as depicted in FIG. 5B) on the package 140 which orients the package 140 and electrical components within so that the electronics may be charged via wire through the port 430. This port 430 may not be needed if a wireless charging application is included in the electrical components. In some embodiments, a wireless charger is provided within the electronics package 140.

Referring now to FIGS. 5A, 5B, and 5C, the package 140 is shown, according to some embodiments. In some embodiments, the package 140 includes a first slot 510, a second slot 520, a positioning structure 530, and an opening 540. A first slot 510 is sized to fit the electronics circuit (not shown) while the second slot 520 is sized to fit a battery that will power the electronics circuit. As shown in FIG. 5B, an opening 540 is made allowing wires to pass between a first slot 510 and a second slot 520. As shown in FIG. 5C, a positioning structure 530 is sized to fit a positioning structure 420 on the body 130 to constrain package 140 in line with port 430, allowing for proper connection between electrode wires passing through cut 250 of the housing 110 and the electronic circuit located in first slot 510.

Figure 6A:
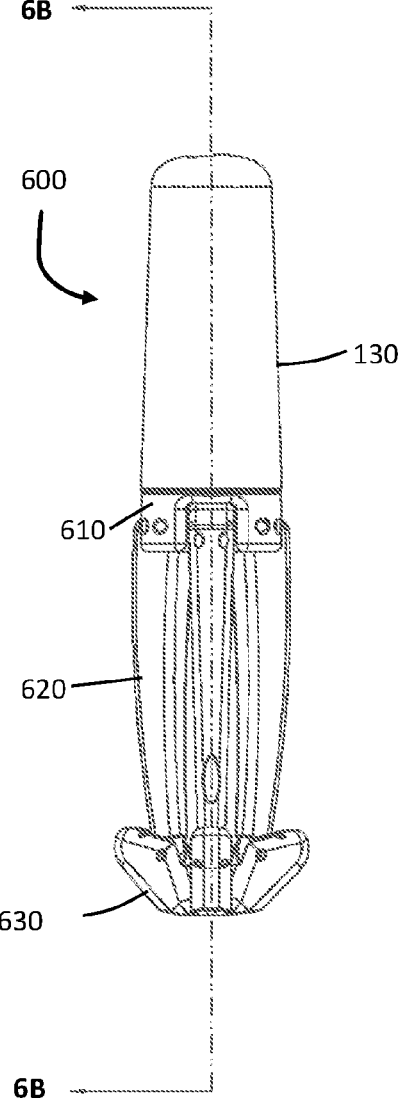
FIG. 6A illustrates a biosignal acquisition device operating as a flexible montage brain monitoring system, according to some embodiments.

Referring to FIG. 6A, an EEG device 600 operating as a flexible montage brain monitoring system is shown, according to some embodiments. The EEG device 600 features a plurality of parts, including a housing 610, legs 620, feet 630 and a body 130. A portion of the housing 610 is inserted through an opening of the body 130, while portions of the legs 620 are inserted into openings in the housing 610. Apertures in the housing 610 and legs 620 are sized to fit a pin to secure a leg 620 in a housing 610 opening. Alternatively, a leg 620 may be secured with an extrusion on the housing 610 (not shown yet) and an additional part to prevent it from sliding off the extrusion on the housing 610 (also not shown yet). An opening in the body 130 may be threaded or secured to the housing 610 using adhesive or a fusing process.

Figure 6B:
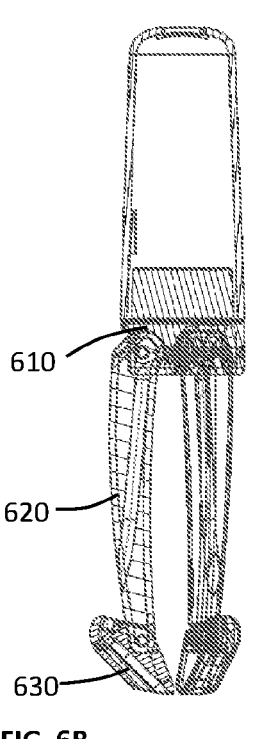
FIG. 6B illustrates a cross-sectional view of the biosignal acquisition device of FIG. 6A along cross-sectional line 6B-6B, according to some embodiments.

As illustrated in FIG. 6B, a cross-sectional view of the EEG device 600 of FIG. 6A along line 6B-6B is shown. Herein, the housing 610 is entered into the body 130 (see FIG. 4) opening. The body 130 is also sized to fit electrical components necessary to record signals and provide portability which sit above the housing 610. The housing 610 openings sized to fit the leg 620 extrusions incorporate a feature design to prevent rotation of the leg 620 past a specified angle. This feature allows for rapid opening and closing of the legs, allowing for quick relocation of electrodes to accommodate multiple montages with minimal adjustment.

Figures 7A, 7B, 7C:
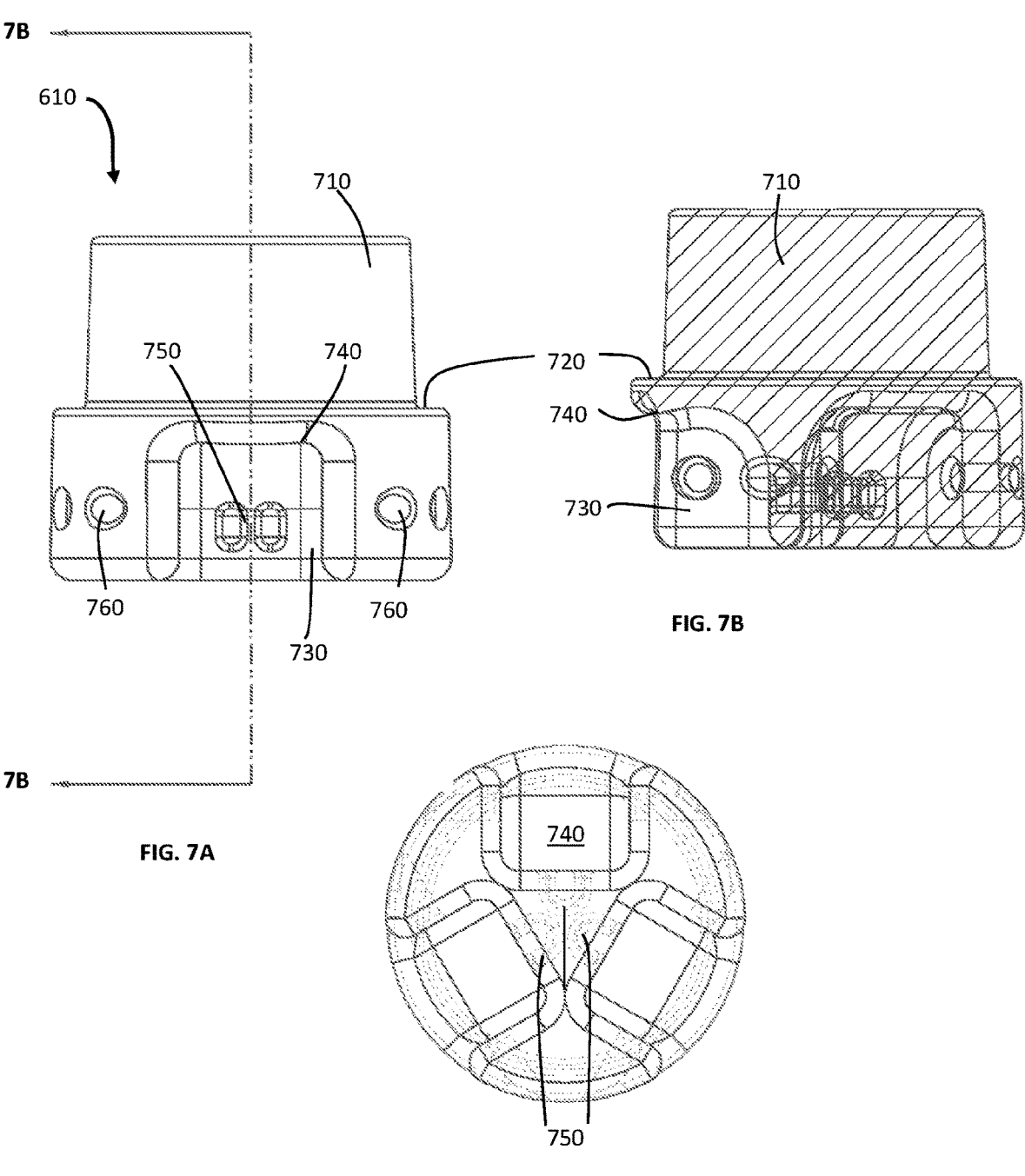
FIG. 7A illustrates a housing of the biosignal acquisition device depicted in FIG. 6A, according to some embodiments.
FIG. 7B illustrates a cross-sectional view of the housing of FIG. 7A taken across line 7B-7B showing a constraining surface, according to some embodiments.
FIG. 7C illustrates a bottom view of the housing of FIG. 7A showing a supporting structure, according to some embodiments.

Referring now to FIG. 7A, the housing 610 is shown, according to some embodiments. In some embodiments, the housing 610 includes an extrusion 710, a constraining surface 720, an opening 730, a second constraining surface 740, a supporting structure 750, and securing points 760. The housing 610 may also include a cut (e.g. 250 as depicted FIG. 2B). The extrusion 710 is sized to fit the opening on the body 130 while the constraining surface 720 serves to limit the entry of housing 610 into the body 130. As shown in FIG. 7B, the opening 730 is sized to fit the leg 620 while the constraining surface 740 fits with an angled surface on the leg 620 to prevent movement or rotation past a specified angle when the leg 620 is fixed to the securing point 760, allowing for rapid switching of the leg 620 between an open or closed position. A supporting structure 750 provides an opening through which a tendon may pass through to control the position of the feet 630 in relation to the housing 610. As shown in FIG. 7C, the supporting structure 750 is shaped to allow a single tendon to pass through and connect to two points on the feet 630. Alternatively, the continuous supporting structure 750 could be represented by two discrete securing points, allowing for either a single tendon to pass through a foot 630, or two tendons run in parallel to one another secured at two discrete points on a foot 630.

Figures 8A, 8B, 8C:
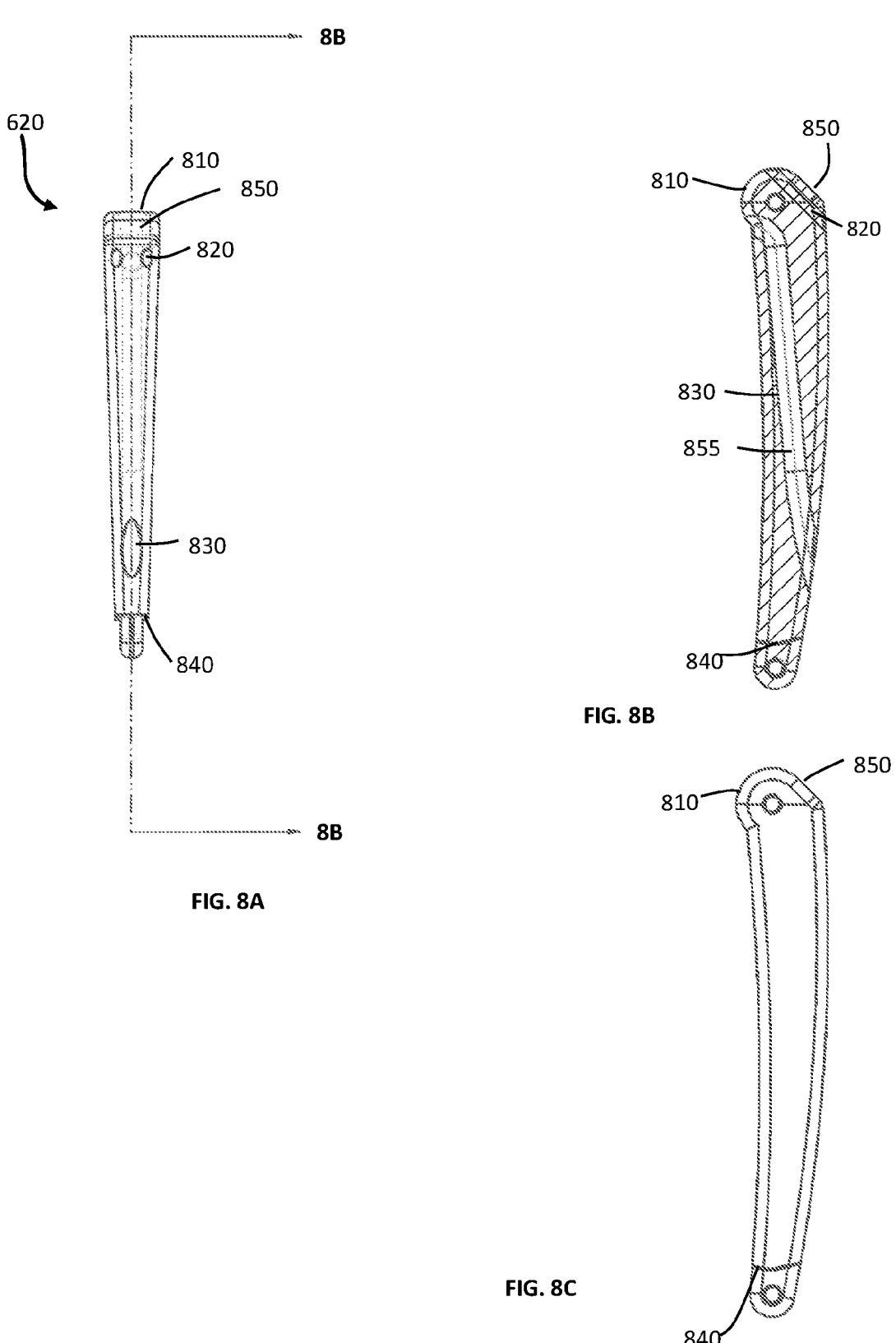
FIG. 8A illustrates a leg of the biosignal acquisition device of FIG. 6A, according to some embodiments.
FIG. 8B illustrates a cross-sectional view of the leg depicted in FIG. 8A taken across line 8B-8B showing a first and second channel, according to some embodiments.
FIG. 8C illustrates a side view of the leg depicted in FIG. 8A showing a constraining surface, according to some embodiments.

Referring now to FIG. 8A, leg 620 is shown, according to some embodiments. The leg 620 may include a rounded surface 810, a first channel 820, a second channel 830, a constraining surface 840 and an angled surface 850. A rounded surface 810 may be sized to fit the opening 730 of the housing 610, allowing the leg 620 to rotate about the rounded surface 810 central axis. The leg 620 is limited by the angled surface 850 and the second constraining surface 740 of the housing 610. When a leg 620 is attached to the housing 610 via a pin through or extrusion from the rounded surface 810 central axis, the angled surface 850 of the leg 620 and the second constraining surface 740 of the housing 610 prevent movement of the leg 620 past a specified angle, allowing for rapid switching of positions to different montages across the scalp with minimal adjustment needed. A constraining surface 840 provides a mechanical stop for the feet 630, limiting the feet 630 to a minimum and maximum angle so that any force necessary to achieve contact will not jeopardize electrode contact with the scalp. As shown in FIG. 8B, a second channel 830 provides a path for an electrode wire to reach the electronic components within the body. A first channel 820 provides a path for the tendon(s) that control the feet position, providing consistent electrode positioning with respect to the housing 610 and patient scalp, allowing for proper contact whether closed or open.

Referring now to FIG. 9A, a foot 630 is shown, according to some embodiments. The foot 630 includes an opening 910, a securing point 920, a cut 930, a constraining surface 940, and a securing point 950. As shown in FIG. 9B, an opening 910 is sized to fit conventional EEG electrode and wires which are routed through a channel 830 of a leg 620. Securing points 920 are sized to retain a tendon wire, which is routed through channels 830 of the leg 620 and then connected to a supporting structure 750 of a housing 610. As shown in FIG. 9C, a cut 930 is sized to fit the distal end of leg 620. A constraining surface 940 prevents rotation past a specified angle and when paired with constraining surface 840 of leg 620 maintains the electrode contact even with a failure of a tendon. A securing point 950 connects the foot 630 to the leg 620 and provides an axis of rotation for the foot 630 with respect to the leg 620, allowing the tendon to control electrode positioning with respect to the housing 610.

Figures 10A, 10B:
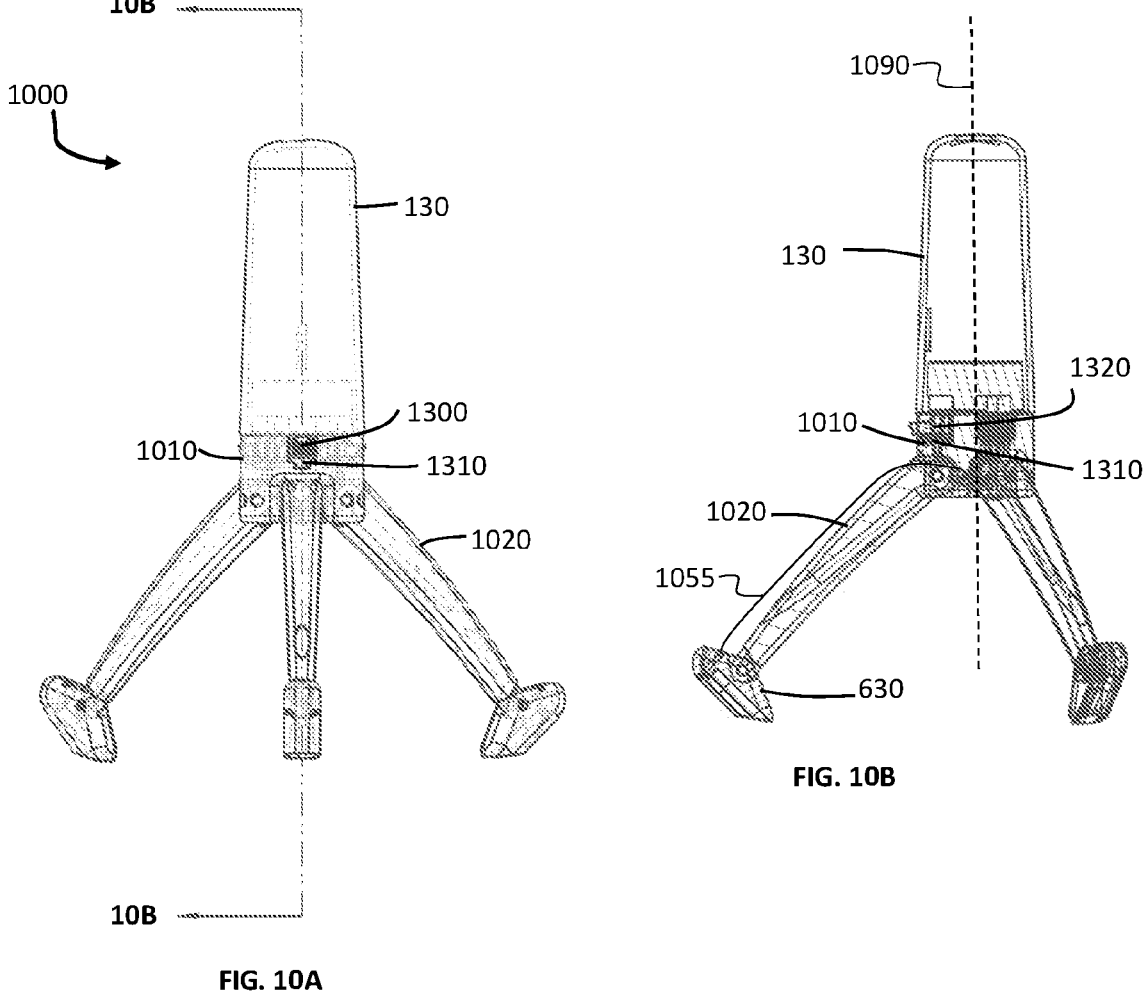
FIG. 10A illustrates a biosignal acquisition device operating as a flexible montage brain monitoring system, according to some embodiments.
FIG. 10B depicts a cross-sectional view of the biosignal acquisition device of FIG. 10A along line 10B-10B, according to some embodiments.

Referring to FIGS. 10A and 10B, an EEG device 1000 operating as a flexible montage brain monitoring system is shown, according to some embodiments. The EEG device 1000 features a plurality of parts, including a housing 1010, securing assembly 1300, legs 1020, feet 630 and a body 130. A portion of the housing 1010 is inserted through an opening of the body 130, while portions of the legs 1020 are inserted into openings in the housing 1010. Apertures in the housing 1010 and legs 1020 are sized to fit a pin to secure a leg 1020 in a housing 1010 opening. Alternatively, at least one of the legs 1020 may be secured with an extrusion on the housing 1010 (not shown yet) and an additional part to prevent it from sliding off the extrusion on the housing 1010 (also not shown yet). An opening in the body 130 may be threaded or secured to the housing 1010 using adhesive or a fusing process.

As illustrated in FIG. 10B, a cross-sectional view of the EEG device 1000 of FIG. 10A along line 10B-10B is shown. Herein, the housing 1010 is entered into the body 130 (see FIG. 4) opening. The body 130 is also sized to fit electrical components necessary to record signals and provide portability which sit above the housing 1010. The housing 1010 openings sized to fit the leg 1020 extrusions incorporate a feature design to prevent rotation of the leg 1020 past a specified angle. The securing assembly 1300 serves to secure the leg 1020 at a plurality of discrete angles which allows for rapid adjustment of leg 1020 positioning, allowing for quick relocation of electrodes to accommodate multiple montages with minimal adjustment.

FIG. 10B also depicts tension-wire or tendon 1055 which is configured to bias a corresponding leg 1020, according to some embodiments. In some embodiments, each leg 1020 is provided with at least one tendon 1055. In some embodiments, each leg is provided with two tendons. In some embodiments, the legs are biased toward a center axis (e.g. 1090) by each of the housing by the corresponding tendons.

Referring now to FIGS. 11A and 11B, a housing 1010 is shown, according to some embodiments. The housing 1010 may include an extrusion 1110, a constraining surface 1120, an opening 1130, a second constraining surface 1140, a supporting structure 1150, securing points 1160, slot 1170, and cut 1180. The housing 1010 may also include a cut (e.g. cut 250 as depicted in FIG. 2B). The extrusion 1110 is sized to fit the opening on the body 130 while the constraining surface 1120 serves to limit the entry of housing 1010 into the body 130. A slot 1170 is sized to fit a securing assembly 1300 with a cut 1180 to allow for a pin to disengage with cuts in a leg 1020 to provide a plurality of discrete angular positions. As shown in FIG. 11B, the opening 1130 is sized to fit the leg 1020 while the constraining surface 1140 fits with an angled surface on the leg 1020 to prevent movement or rotation past a specified angle when the leg 1020 is fixed to the securing point 316, allowing for rapid switching of the leg 1020 between plurality of discrete positions. A supporting structure 1150 provides an opening through which a tendon may pass through to control the position of the feet 630 in relation to the housing 1010. As shown in FIG. 11C, the supporting structure 1150 is shaped to allow a single tendon to pass through and connect to two points on the feet 630. Alternatively, the continuous supporting structure 1150 could be represented by two discrete securing points, allowing for either a single tendon to pass through a foot 630, or two tendons run in parallel to one another secured at two discrete points on a foot 630. A cut 1180 provides access of so a pin may engage with the leg, stopping its rotation at a plurality of discrete positions.

Figures 12A, 12B:
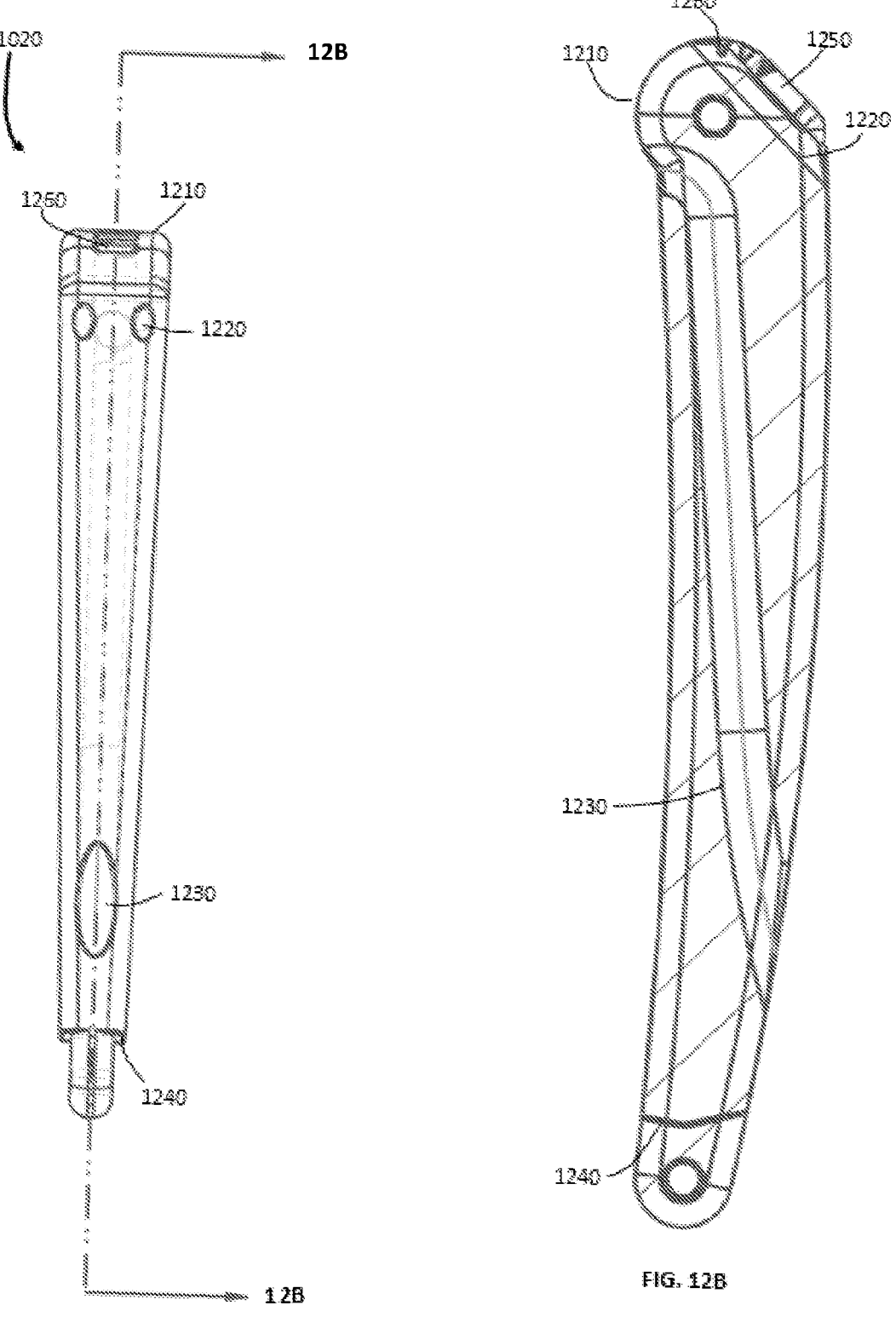
FIG. 12A shows the leg of the biosignal acquisition device of FIG. 10A, according to some embodiments.
FIG. 12B is a cross-sectional view of the leg depicted in FIG. 12A taken along line 12B-12B showing a first and second channel, according to some embodiments.

Referring now to FIGS. 12A and 12B, a leg 1020 is shown, according to some embodiments. The leg 1020 may include a rounded surface 1210, a first channel 1220, a second channel 1230, a constraining surface 1240, an angled surface 1250 and cuts 1260. A rounded surface 1210 is sized to fit the opening 1130 of the housing 1010, allowing the leg 1020 to rotate about the rounded surface 1210 central axis. The leg 1020 is limited by the angled surface 1250 and the second constraining surface 1140 of the housing 1010. When a leg 1020 is attached to the housing 1010 via a pin through or extrusion from the rounded surface 1210 central axis, the angled surface 1250 of the leg 1020 and the second constraining surface 1140 of the housing 1010 prevent movement of the leg 1020 past a specified angle, allowing for rapid switching of positions to different montages across the scalp with minimal adjustment needed. A constraining surface 1240 provides a mechanical stop for the feet 630, limiting the feet 630 to a minimum and maximum angle so that any force necessary to achieve contact will not jeopardize electrode contact with the scalp. As shown in FIG. 12B, a second channel 1230 provides a path for an electrode wire to reach the electronic components within the body. A first channel 1220 provides a path for the tendon(s) that control the feet position, providing consistent electrode positioning with respect to the housing 1010 and patient scalp, allowing for proper contact whether closed or open. Cuts 1260 provide an opening for the pin of securing assembly 1300 to engage with the leg 1020, providing discrete angular positions for the leg 1020 where force may be applied without change the leg 1020 position.

Figure 13A:
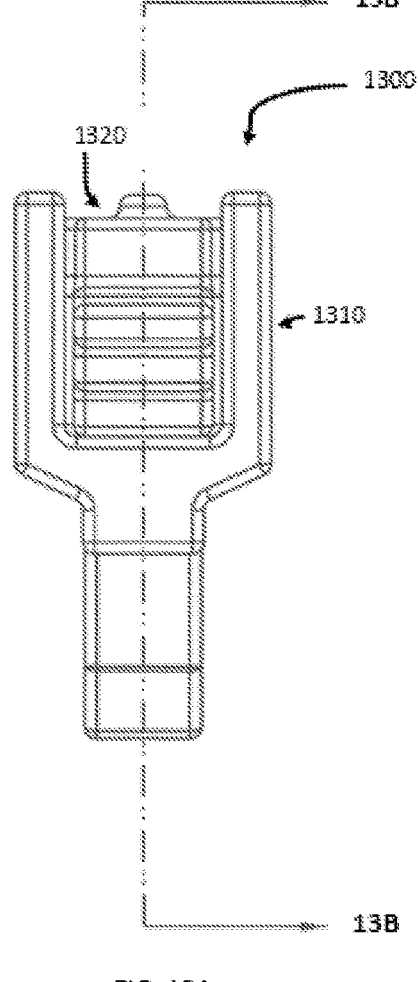
FIG. 13A illustrates a securing assembly, according to some embodiments.
Figure 13B:
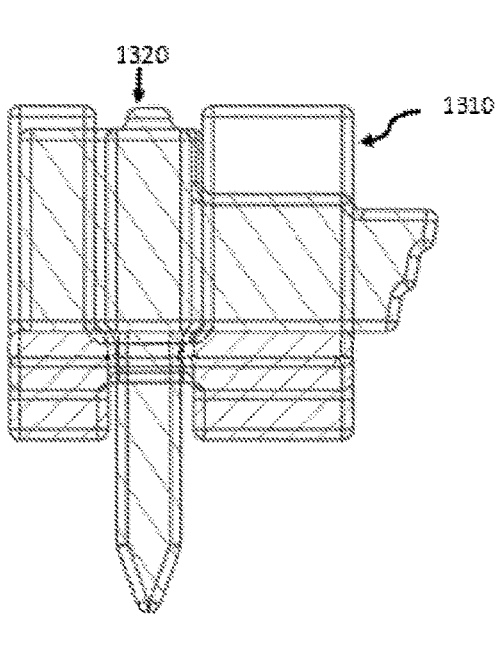
FIG. 13B is a cross-section view of the securing assembly of FIG. 13A taken along line 13A-13A and showing a pin residing within a fixture for locating the pin 1320 as it engages and disengages with a leg of the EEG device, according to some embodiments.

Referring now to FIG. 13A, a securing assembly 1300 is shown, according to some embodiments. The securing assembly 1300 may include a fixture 1310 and a pin 1320. This securing assembly 1300 is sized to fit a slot 1170 of a housing 1010 and is configured to engage with the leg 1020 to prevent motion at a plurality of discrete angles. This allows for a plurality of electrode positions for each leg 1020 and foot 630 connection while maintaining electrode positioning with the tendon actuated foot 630. As shown in FIG. 13B, a pin 1320 is configured to sit within a fixture 1310 which may serve to locate a pin 1320 as it engages and disengages with a leg 1020.

Figure 14A:
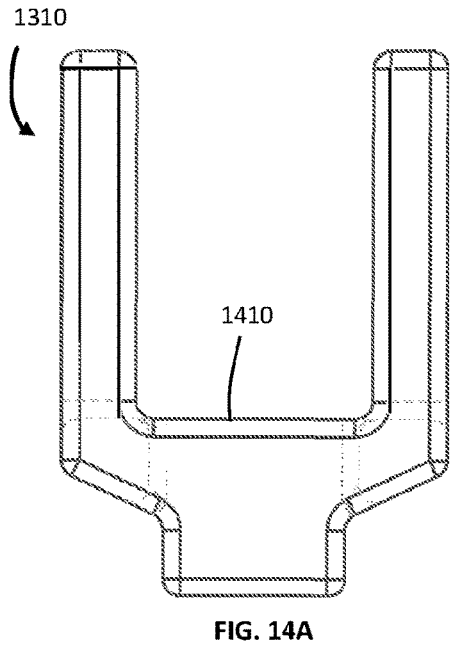
FIG. 14A illustrates a fixture, according to some embodiments.
Figure 14B:
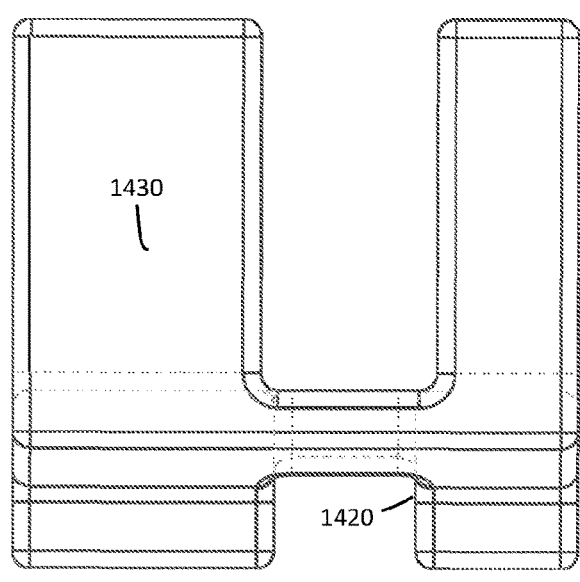
FIG. 14B illustrates a side view of the fixture of FIG. 14A showing a cut and supporting structure.

Referring now to FIGS. 14A and 14B, a fixture 1310 is shown, according to some embodiments. In some embodiments, the fixture 1310 includes an opening 1410, a cut 1420, and a supporting structure 1430. The opening 1410 is sized to fit a controlling structure 1510 (see FIG. 15A) of the pin 1320 which allows for the pin 1320 to fit within the fixture 1310 and be controlled by a finger or mechanism. As shown in FIG. 14B, the cut 1420 is sized to fit an extrusion

1520 (see FIG. 15A) of the pin 1320, which allows the extrusion 1520 of pin 1320 to pass through the cut 1420 and engage with the cuts 1260 of leg 1020. The supporting structure 1430 is sized to fit a locating structure 1530 (see FIG. 15A) on the pin 1320 which allows for the pin 1320 to move up and down without changing orientation as the extrusion 1520 of the pin 1320 engages and disengages from the cuts 1260 on leg 1020.

Figure 15A:
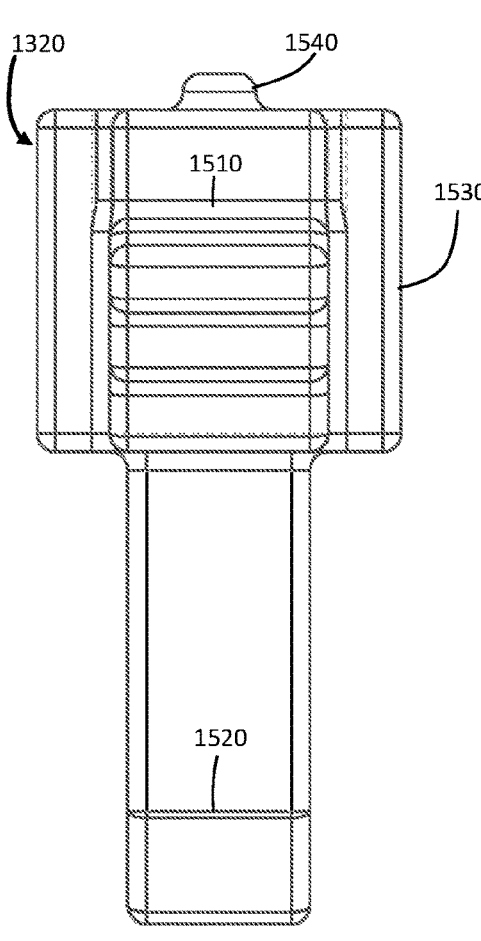
FIG. 15A illustrates a pin, according to some embodiments.
Figure 15B:
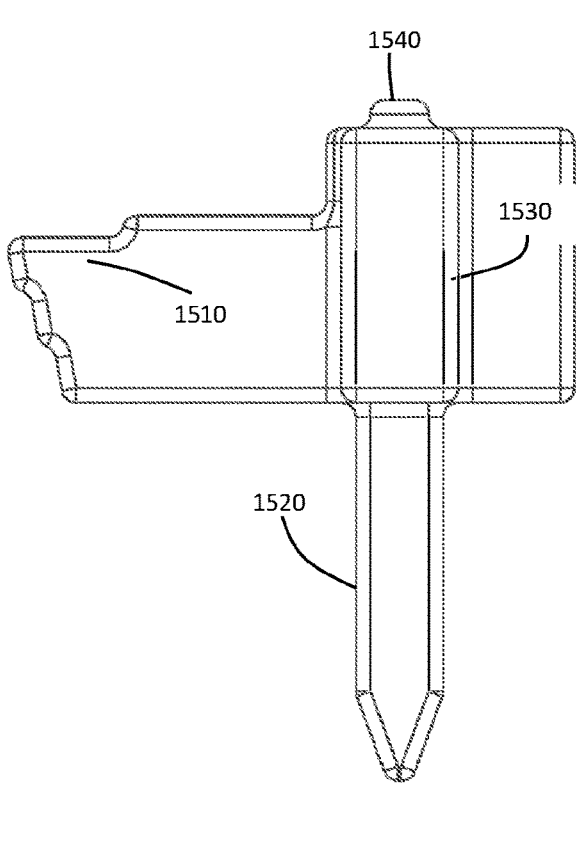
FIG. 15B illustrates a side view of a pin showing a controlling structure and an extrusion, according to some embodiments.

Referring now to FIGS. 15A and 15B, a pin 1320 is shown, according to some embodiments. In some embodiments, the pin 1320 include the controlling structure 1510, the extrusion 1520, at the locating structure 1530, and a securing point 1540. The controlling structure 1510 serves to allow for control of the vertical location of the pin 1320 sitting within a fixture 1310 by a user finger or mechanism. The extrusion 1520 is sized to pass through the cut 1420 of the fixture 1310, which is configured to engage with cuts 1260 of leg 1010 to prevent rotation of the leg 1010 when engaged to provide a plurality of discrete angular positions. The locating structure 1530 is sized to fit the supporting structure 1430 of the fixture 1310, which is configured to maintain orientation as pin 1320 is moved up and down within the opening 1410 of the fixture 1310 by the controlling structure 1510 of the pin 1320. The securing point 1540 is configured to engage with a spring to direct a pin 1320 back into a state where after raising pin 1320 to rotate leg 1010, extrusion 1520 is once again engaged with cuts 1260 of leg 1010.

Figure 16:
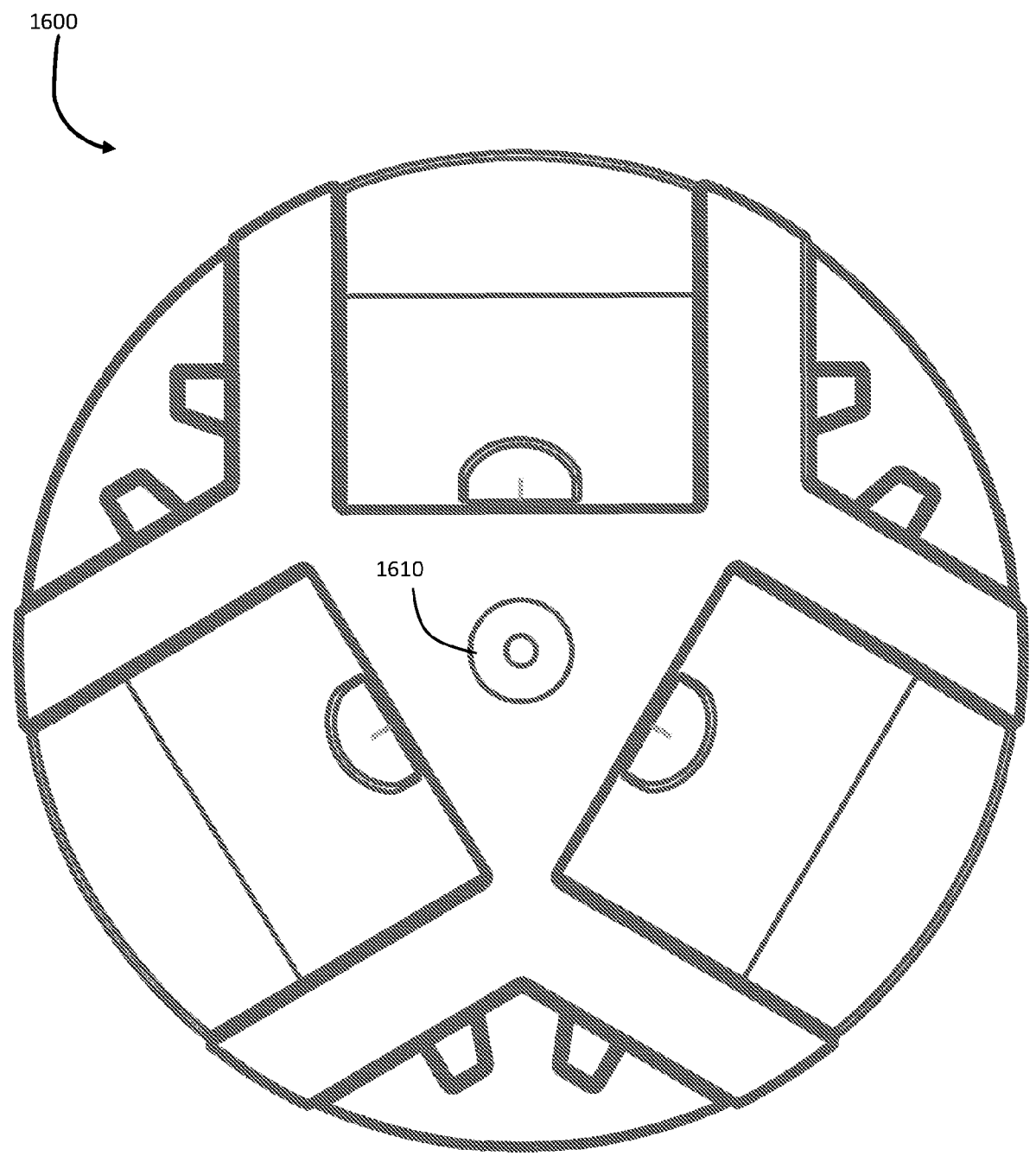
FIG. 16 illustrates a housing that includes a camera 1610, according to some embodiments.

As shown in FIG. 16, the housing 1600 includes a camera 1610, according to some embodiments. This camera 1610 is configured to be utilized by image processing algorithms in a software application to locate the housing with respect to the patient's scalp. This provides a metric to verify that users are placing electrodes on the specified montages needed to provide assessment with minimal electrodes needed. The system may utilize accelerometers or gyroscopes with or without the camera component. There may be accelerometers or gyroscopes in the legs or electrodes to assist in tracking the device position in space as users are navigating the scalp.

Figures 17A, 17B:
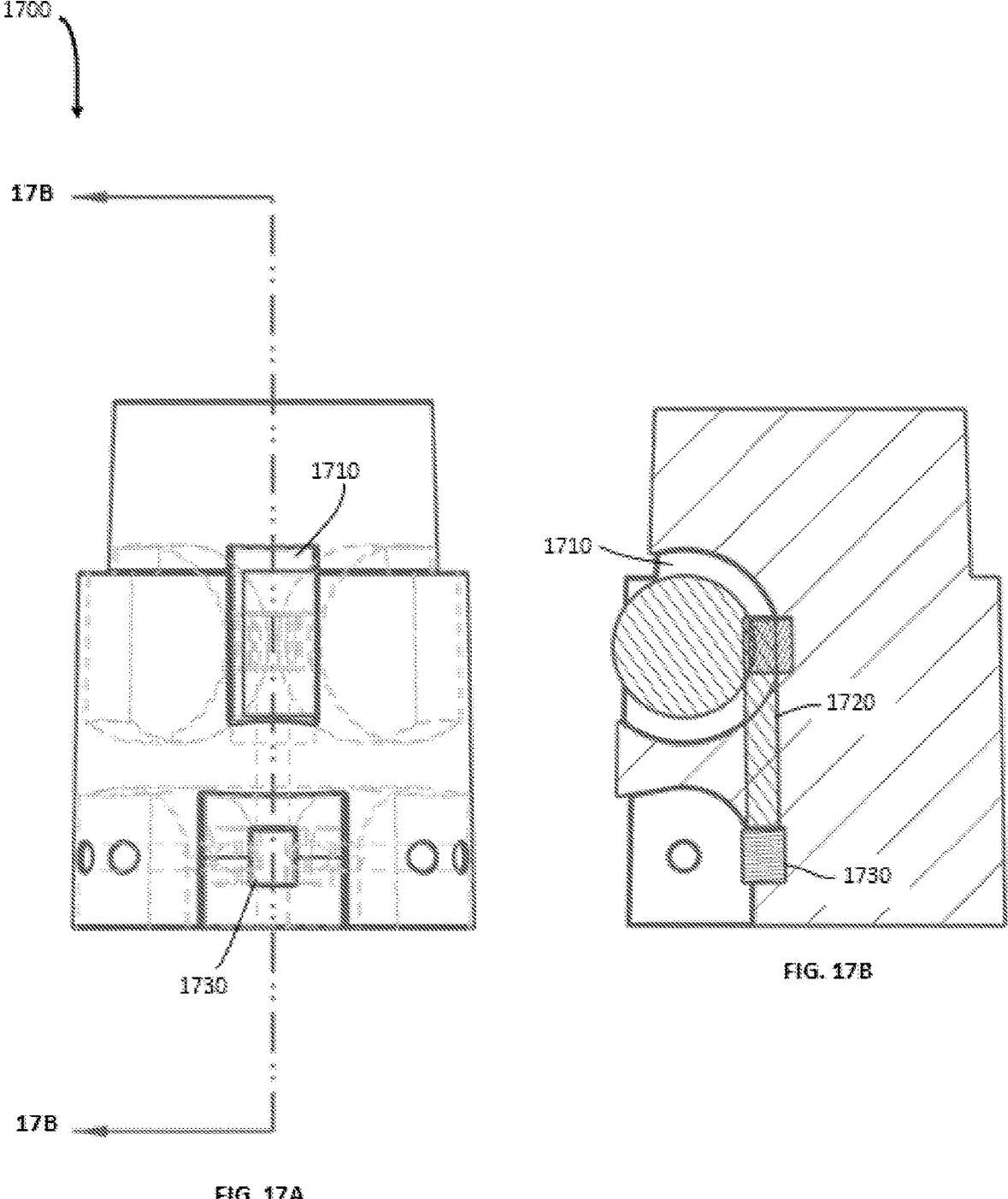
FIG. 17A depicts a gear housing, according to some embodiments.
FIG. 17B is a cross section view the gear housing depicted in FIG. 17A taken across line 17B-17B, according to some embodiments.

As shown in FIGS. 17A and 17B, a gear housing is depicted, according to some embodiments. This gear housing includes a gearset (1710, 1720, 1730). The gearset may provide a mechanism for controlling the legs using a user's finger or motor. The gearset may be applied to each individual leg or to a plurality of legs at the same time. Depending on which application of the gearset, each leg may be controlled independently of each other or may synchronize the movement of each leg with respect to the other legs. The gearset when paired with a motor will not require user force to move the leg position, and instead will utilize physical button presses on the device or digital button presses on the software application. In some embodiments, the gearset and legs attached, would be adjusted automatically depending on the amount of force that is applied to each leg. In some embodiments, there would be pressure/force sensors located either at the electrode, at the leg, or within the housing. When collecting the force data and impedance data (measured through the electrical components and software application), the software will be able to adjust the legs to match experimentally determined specifications to provide required contact impedance for signal integrity with minimal user input.

Figures 18A, 18B:
FIG. 18A illustrates a spring-loaded housing, according to some embodiments.
FIG. 18B illustrates a spring-loaded housing with the leg in an open position, according to some embodiments.

As shown in FIGS. 18A and 18B, a spring-loaded housing 1800 is depicted, according to some embodiments. This spring-loaded housing 1800 may include a first cut 1810, a rail 1820, a spring 1830, and a second cut 1840. A first cut 1810 may be sized to fit a leg 1900 to allow for a pin 1910 of the leg 1900 to move along a rail 1820, directing the leg 1800 from a compact position FIG. 17A) to an open position (FIG. 17B). The movement may be driven by a spring 1830, which attaches to an extrusion 1920 of leg 1900. The spring 1830 may provide downward force on an extrusion 1920 of the leg 1900, allowing it to quickly deploy into an open position. This functionality exists to provide an instant deploying device for use in emergency situations. Hence, no user input may be required, except from clicking the deploy button to provide an EEG system when and wherever needed. In place of a spring 1830, the leg 1900 may be driven by an actuator or pulley system.

Figure 19:
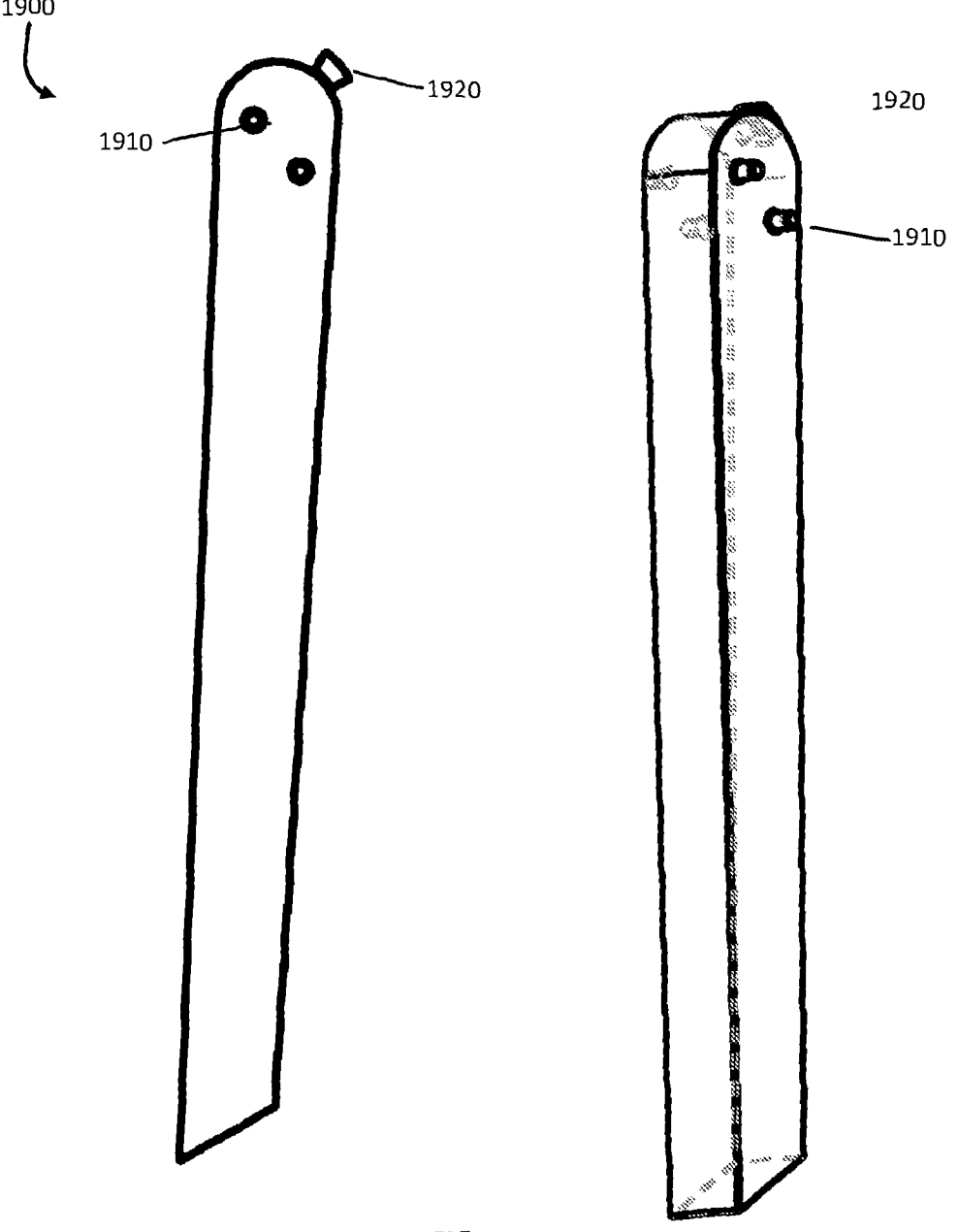
FIG. 19 illustrates a leg with pins and extrusion, according to some embodiments.

FIG. 19 provides an exemplary illustration of the leg 1900 with pins 1910 and extrusion 1920, according to some embodiments. The pin 1910 may be sized to fit rail 1820, providing a path of movement for the leg 1900. This may allow for a more compact version of the device where the leg 1900 is withdrawn into the first cut 1810 of housing 1800 and ejected into the correct position using spring tension. This design may take up less space and can be administered with minimal electronic or user intervention.

Figure 20:
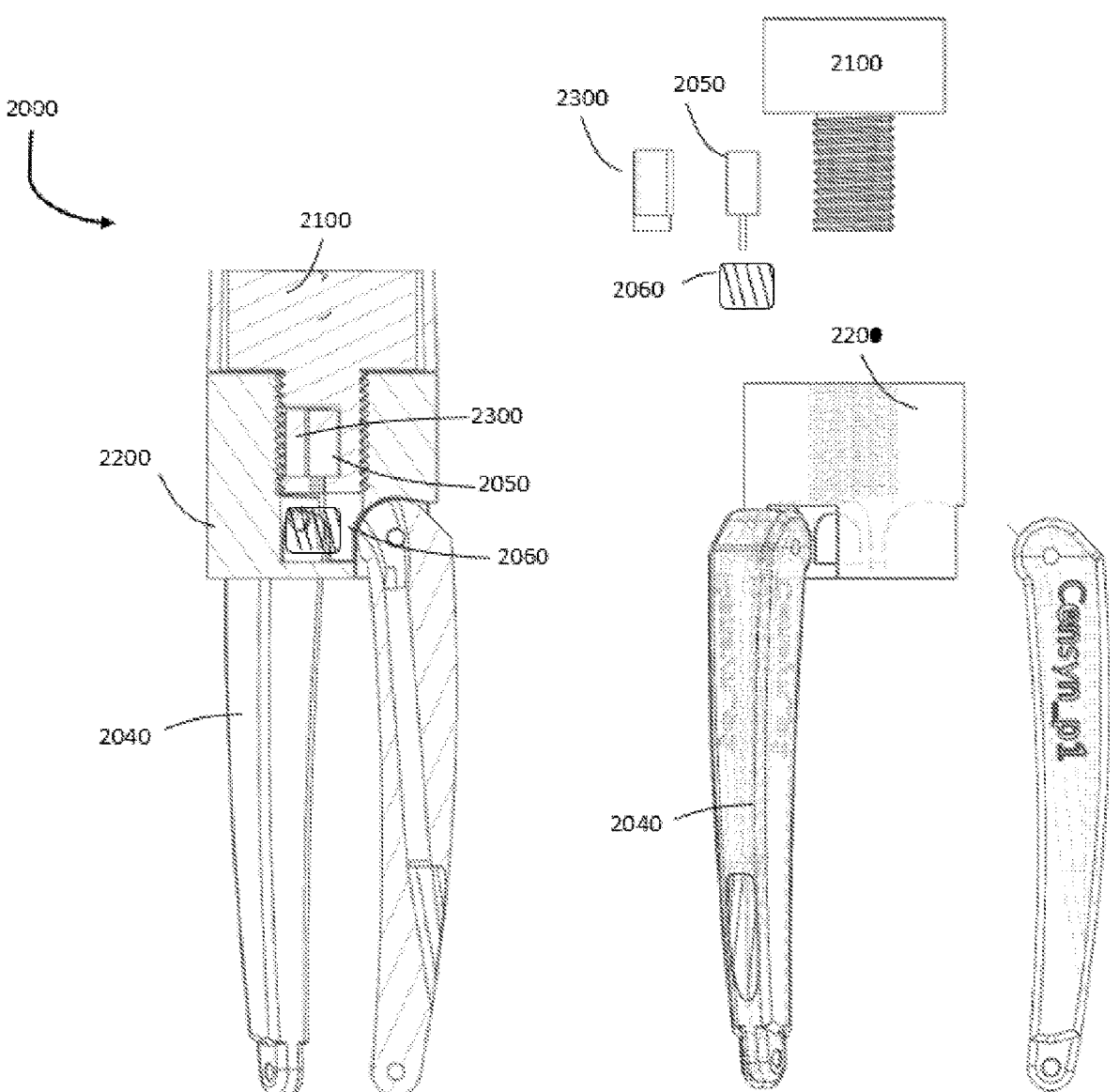
FIG. 20 illustrates a housing encompassing a rotary actuator that is configured to move a gear to rotate a leg, according to some embodiments.

FIG. 20 illustrates a housing 2000 including a top housing 2100, base 2200, leg 2040, motor 2050 and gear 2060, according to an embodiment. In some embodiment, the top housing 2100 is threaded and sized to fit the base 2200. Within the top housing 2100 sits a motor 2050 and cover 2300. In some embodiments, the motor 2050 shaft fits into a gear 2060 which will interface with the leg 2040 to open and close when power is applied to the motor 2050.

Figure 21:
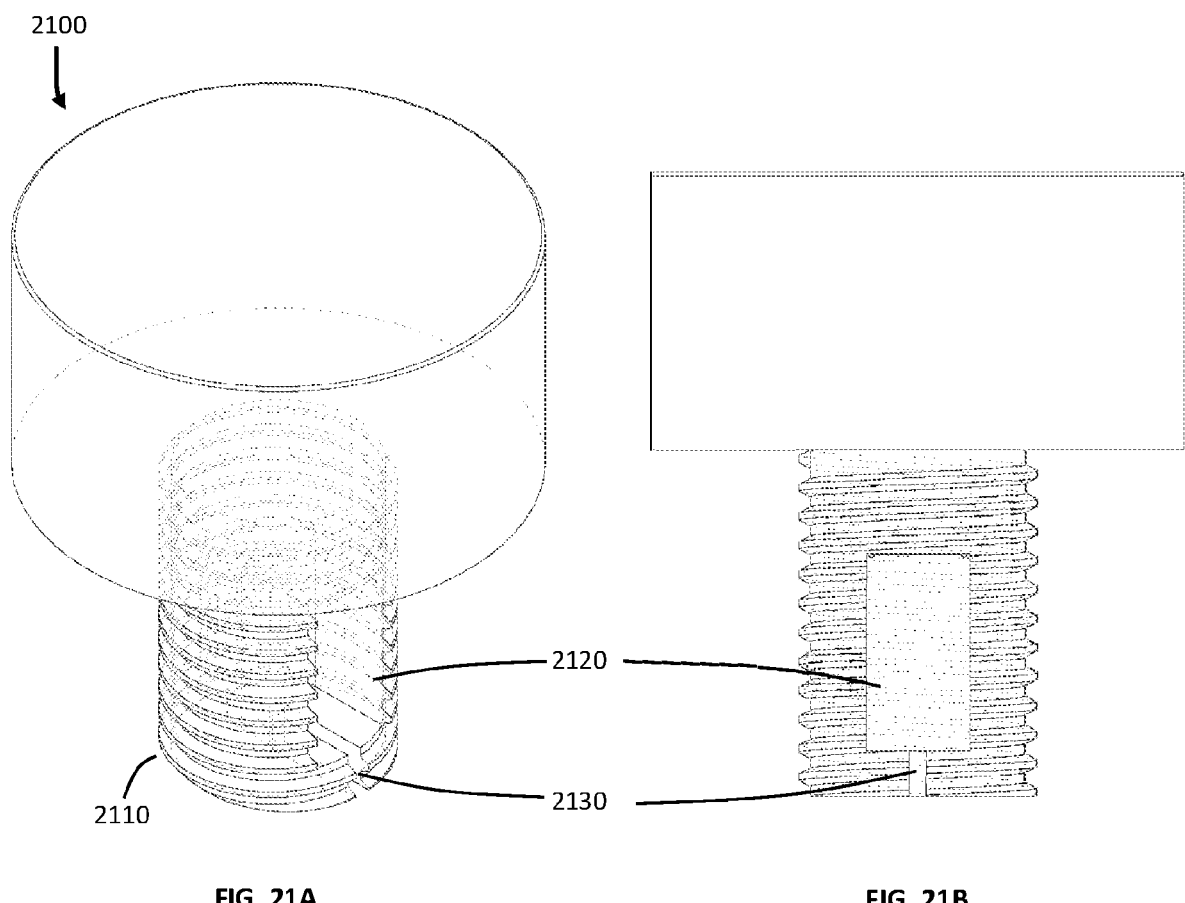
FIG. 21A illustrates a top housing which contains rotary actuator, according to some embodiments.
FIG. 21B illustrates a front view of top housing which contains rotary actuator, according to some embodiments.

FIGS. 21A and 21B illustrates a top housing 2100 which is comprised of an extrusion 2110 sized to fit within the cut 2210 of base 2200, according to some embodiments. In some embodiments, a threaded mechanism is used to secure the top housing 2100 into the base 2200, however other fixation techniques may be used, such as friction fit and laser adhesion. A first cut 2120 and a second cut 2130 may be sized to fit the motor 2050 and its rotary shaft to allow for rotation of the gear 2060. First cut 2120 may be sized to fit cover 2300 which is designed to stabilize the motor 2050 in position for consistent application of gear 2060 to leg 2040.

Figure 22:
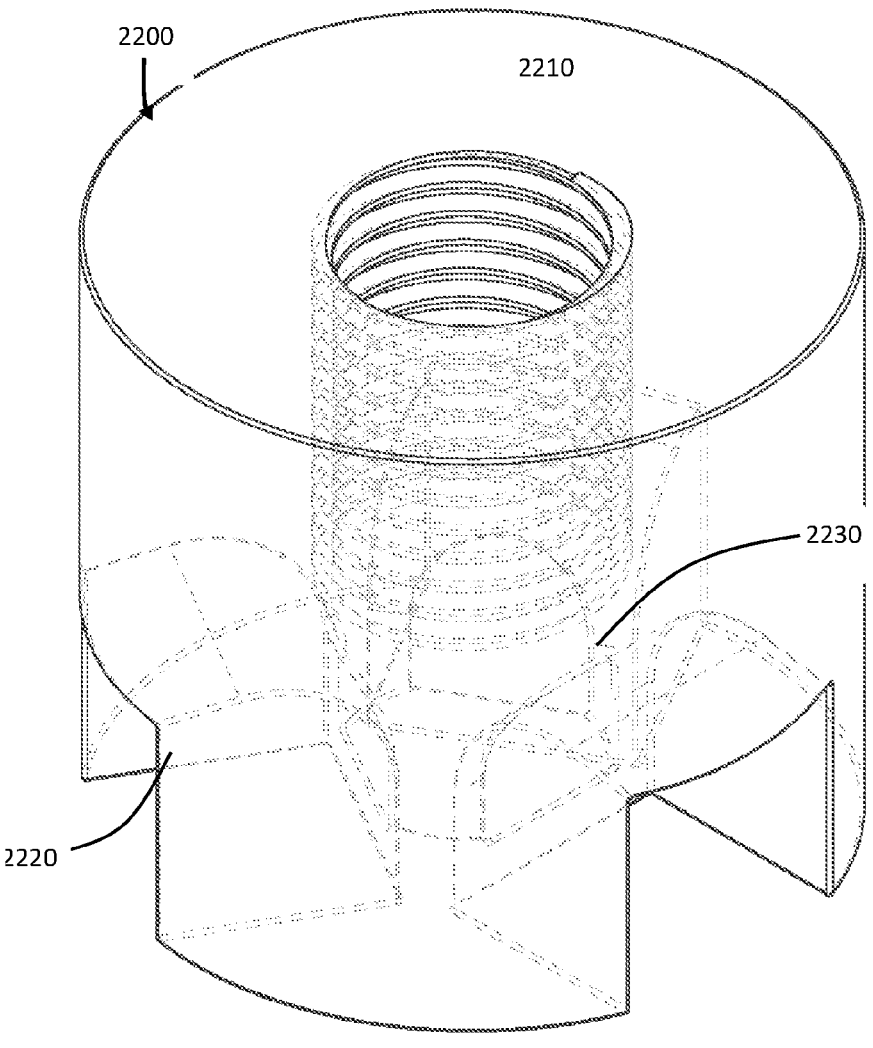
FIG. 22 illustrates an isometric view of a base which serves to hold rotary actuator and legs, according to some embodiments.

FIG. 22 illustrates a base 2200 which is comprised of a first cut 2210 sized to fit the extrusion 2110 of top housing 2100, according to some embodiments. A second cut 2220 may be sized to fit the leg 2040 and a third cut 2230 provides an opening for the gear 2060 to engage with the leg 2040, translating the rotary motion of the gear 2060 into opening or closing of the leg 2040.

Figure 23:
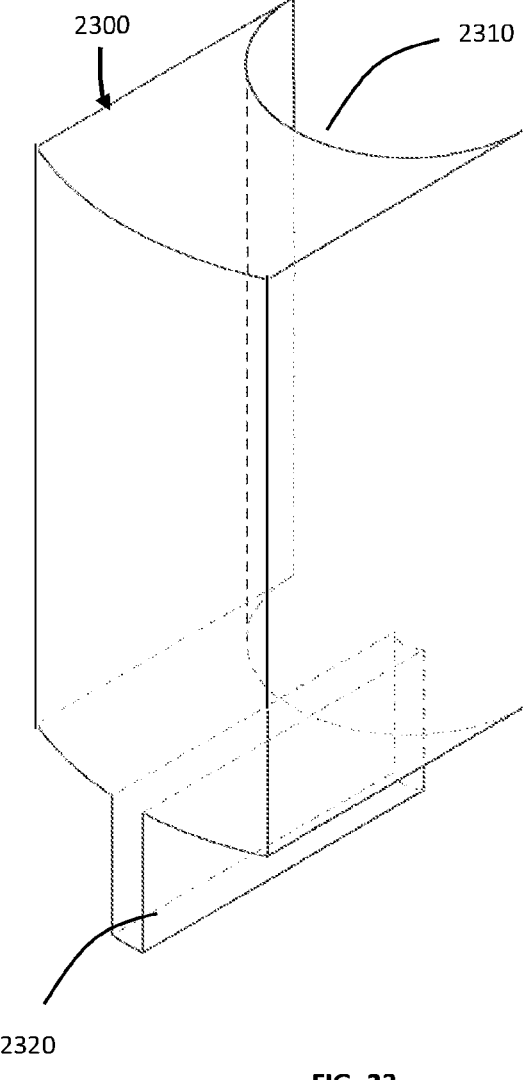
FIG. 23 illustrates an isometric view of cover to protect rotary actuator and keep it fixed, according to some embodiments.

FIG. 23 illustrates a cover 2300 which is comprised of a first cut 2310 sized to fit the motor 2050, according to some embodiments. An extrusion 2320 may be sized to fit the second cut 2130 of top housing 2100. The cover 2300 may keep the motor and shaft in position during operation so the gear may consistently engage with leg to translate rotary movement to angular displacement.

FIGS. 24A and 24B depicts a pen assembly 2400 which is comprised of housing 2500, driver 2600, translator 2700, constraining body 2800 and leg 2900. In some embodiments, a hand-driven, rotational method of opening and closing the legs 2900 is provided. In some embodiments, a user rotates driver 2600, translator 2700 translates rotation into axial movement and acts upon leg 2900 to change its angle.

Figure 25A:
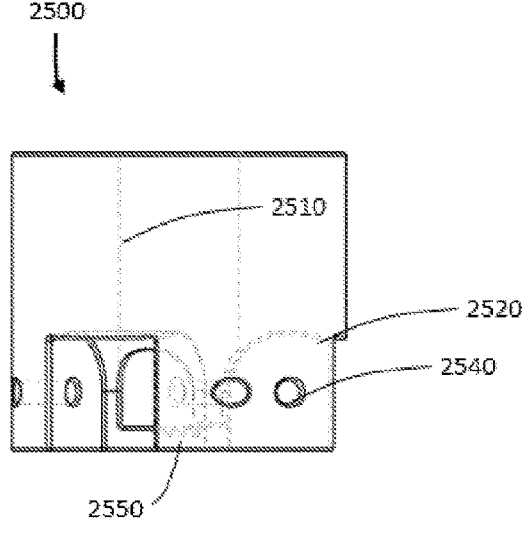
FIG. 25A illustrates a right view of a housing to hold legs to be driven by user rotation of driver, according to some embodiments.
Figure 25B:
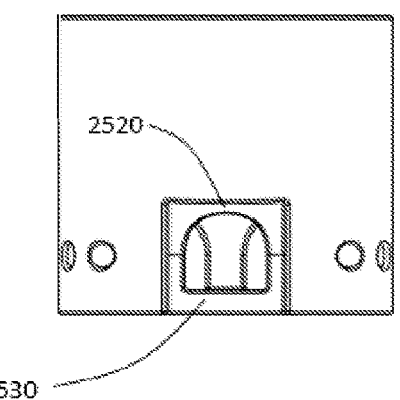
FIG. 25B illustrates a front view of a housing encompassing a cut to hold legs, according to some embodiments.

FIGS. 25A and 25B depict a housing 2500 including first cut 2510, second cut 2520, third cut 2530, holes 2540 and securing cut 2550, according to some embodiments. A first cut 2510 may be sized to fit translator 2700 as it changes position based on driver 2600 rotation, changing angle of legs 2900. A second cut 2520 may be sized to fit leg 2900 and provide a physical constraint to limit its motion to a desired angle. A third cut 2530 may provide an opening for extrusion 2910 of leg 2900 to engage with surface 2730 of translator 2700. Holes 2540 may serve as a common axis about which leg 2900 rotates. Securing cut 2550 is sized to fit securing extrusion 2820 of constraining body 2800.

Figures 26A, 26B:
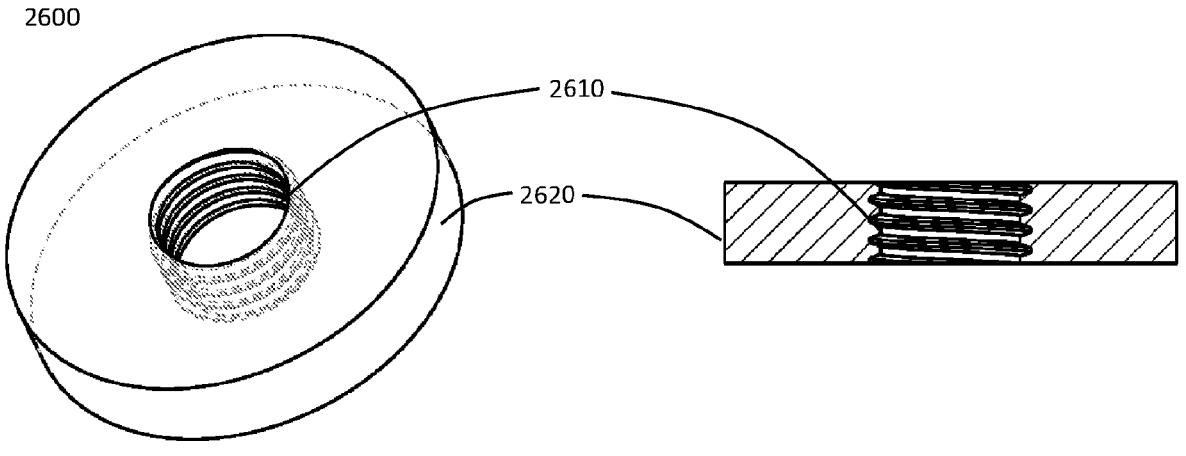
FIG. 26A illustrates an isometric view of driver which rotates a translator, according to some embodiments.
FIG. 26B illustrates a cross section view of driver showing inner threads, according to some embodiments.

FIGS. 26A and 26B illustrates a driver 2600 comprised of inner thread 2610 and outer surface 2620, according to some embodiments. Inner thread 2610 may interface with outer thread 2710 of translator 2700 to change translator 2700 position and leg 2900 angle. In some embodiments, as a user contacts the outer surface 2620 and rotates translator 2600, inner thread 2610 will cause translator 2700 to change position and press against extrusion 2910 of leg 2900.

FIGS. 27A and 27B depict a translator 2700 which is comprised of outer thread 2710, inner cut 2720 and surface 2730, according to some embodiments. In some embodiments, outer thread 2710 is sized to interface with inner thread 2610 of driver 2600 which facilitates translator 2700 movement when driver 2600 is rotated by user. Inner cut 2720 may be sized to allow securing extrusion 2820 of constraining body 2800 to engage with securing cut 2550 of housing 2500 without interference. In some embodiments, a surface 2730 contacts extrusion 2910 of leg 2900 as translator 2700 axial position is changed by user rotation of driver 2600, changing leg 2900 angle.

Figures 28, 29:
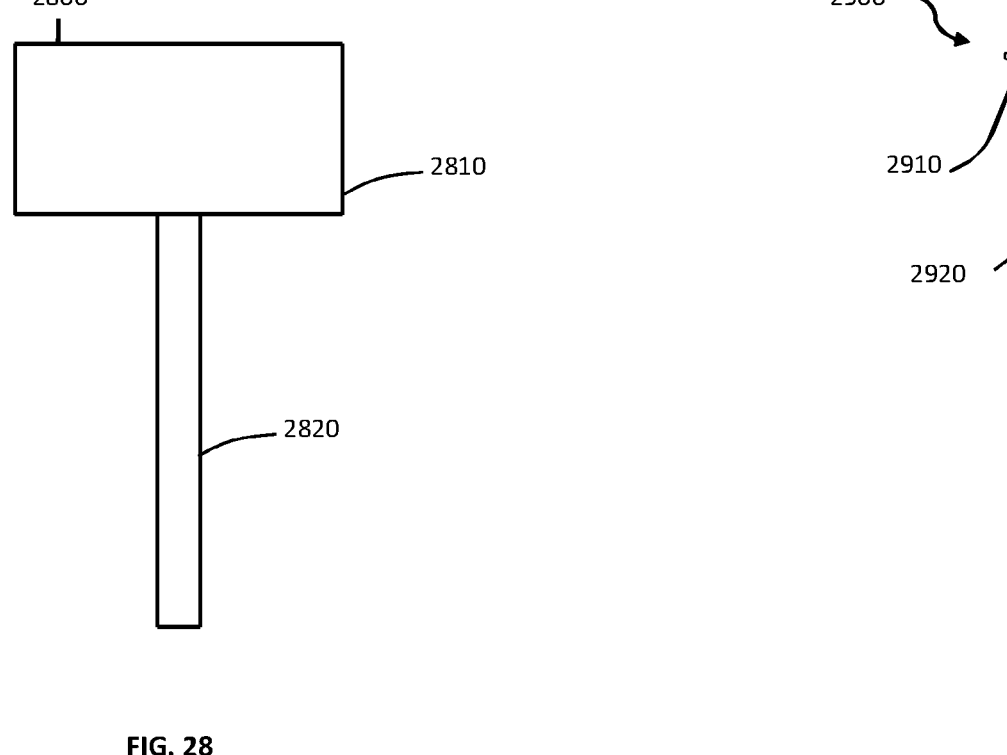
FIG. 28 illustrates a front view of constraining body which serves to maintain assembly, according to some embodiments.
FIG. 29 illustrates a front view of leg including extrusion and hole, according to some embodiments.

FIG. 28 depicts a constraining body 2800 which is comprised of foundation 2810 and securing extrusion 2820, according to some embodiments. In some embodiments, a foundation 2810 provides a surface on which an electronics covering can sit and prevents constraining body 2800 from being encompassed by driver 2600 and translator 2700. In some embodiments, securing extrusion 2820 passes through inner thread 2610 of driver 2600 and inner cut 2720 of translator 2700 to engage with securing cut 2550 of housing 2500. In some embodiments, securing extrusion 2820 may snap into securing cut 2550 of housing 2500 or may be fixed with an adhesive on assembly.

FIG. 29 depicts a leg 2900 which is comprised of extrusion 2910 and hole 2920, according to some embodiments. In some embodiments, extrusion 2910 passes through third cut 2530 of housing 2500 to engage with surface 2730 of translator 2700. As driver 2600 is rotated and translator 2700 changes position, surface 2730 applies translated force to extrusion 2910 which opens and closes the leg 2900. Leg 2900 opens and closes as the translated force on extrusion 2910 provides a moment about hole 2920 axis and causes rotation, changing angle about assembled housing 2400 central axis.

Figures 30A, 30B:
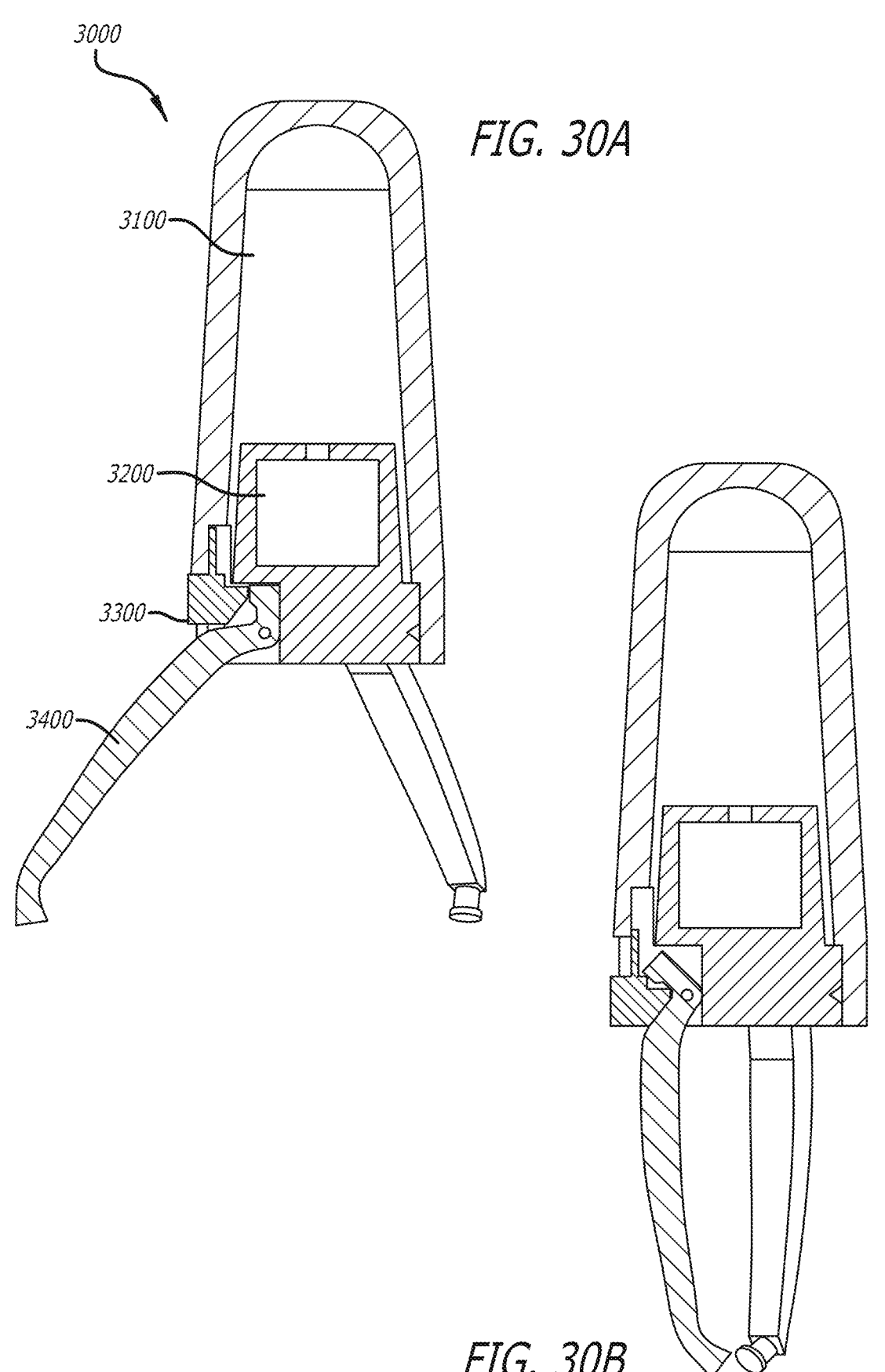
FIG. 30A illustrates a cross section view of a slider driven housing assembly where the slider is in the open position.
FIG. 30B illustrates a cross section view of a slider driven housing assembly where the slider is in the closed position, according to some embodiments.
Figure 34:
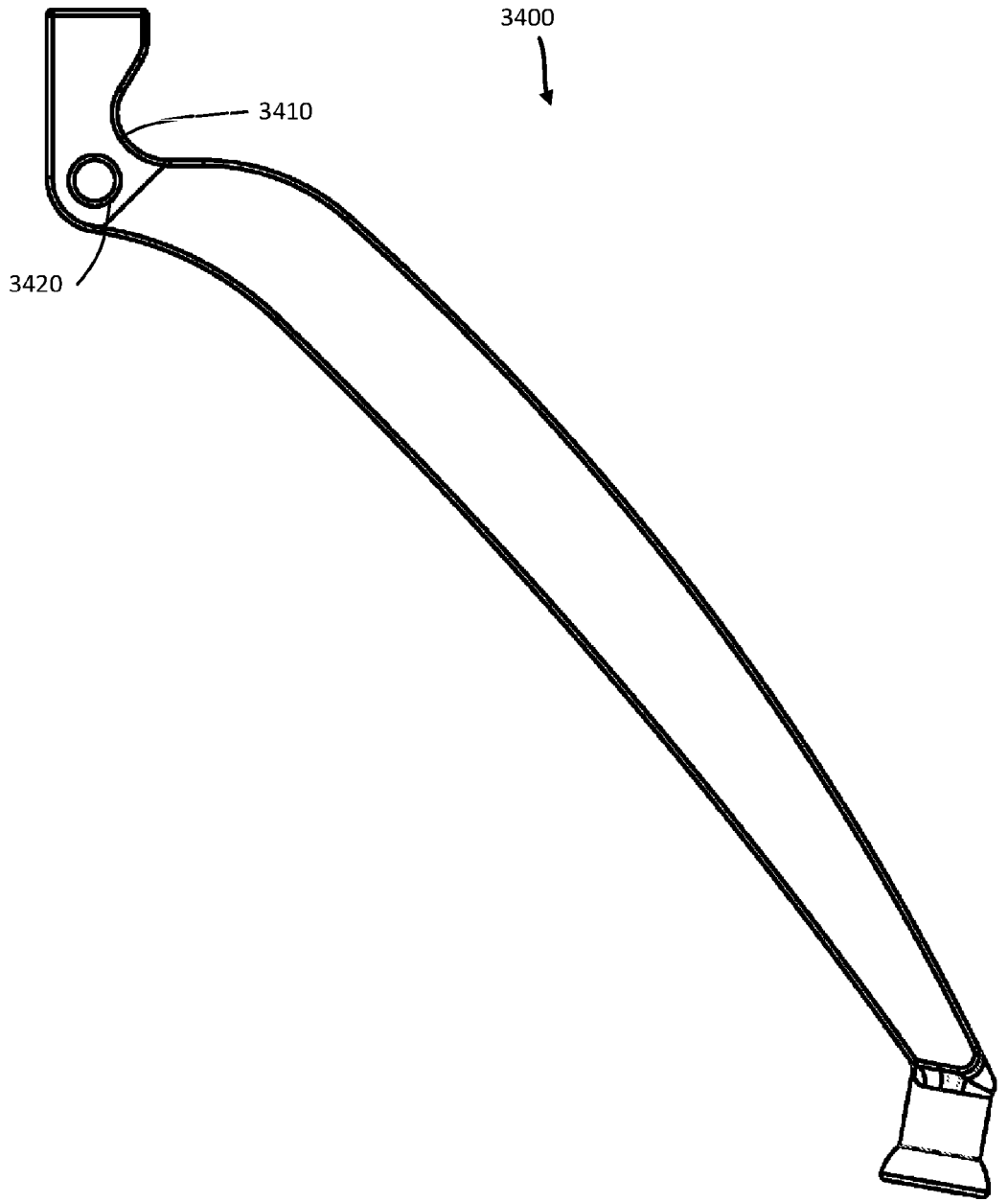
FIG. 34 illustrates a side view of leg including internal cut for slider and hole providing a rotation axis, according to some embodiments.

FIGS. 30A and 30B illustrate an assembled housing 3000 including a body 3100, housing 3200, slider 3300, and a leg 3400, wherein the interaction between a cut (3410 as depicted in FIG. 34) and the slider 3300 allow for a switch-based or sliding opening system. In FIG. 30A, the slider 3300 is in a position which allows the leg 3400 to open, where the electrode can collect signals from the patient. In FIG. 30B, the slider 3300 is in the closed position, where the leg 3400 is not able to open without moving the slider 3300. This system may provide a lightweight mechanism for controlling the operation of the pen. In some embodiments, the mate between the leg and the switch cause the leg to lock in an open and closed position. In some embodiments, a friction fit between the leg and the switch allows for position retention at various placements between the open and closed positions.

Figure 31A:
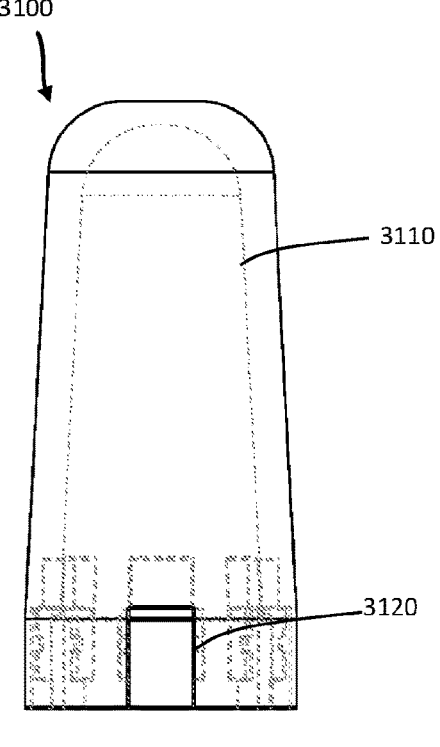
FIG. 31A illustrates a front view of a body with cuts to locate slider, according to some embodiments.
Figure 31B:
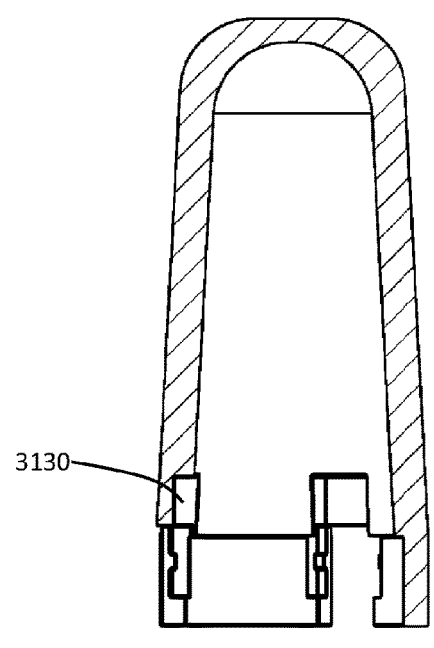
FIG. 31B illustrates a cross section view of a body showing internal cuts, according to some embodiments.

FIGS. 31A and 31B depict a body 3100 to enclose components which is comprised of an opening 3110, a slider cut 3120, and an internal cut 3130, according to some embodiments. In some embodiments, opening 3110 is sized to fit extrusion 3210 of housing 3200. In some embodiments, slider cut 3120 is sized to fit slider 3300 allowing movement of slider 3300 to open and close the legs 3400. In some embodiments, internal cut 3130 is produced with features that allow the slider 3300 to move freely within a range of motion while keeping a slider 3300 between body 3100 and housing 3200. In some embodiments, the internal cut 3030 has features to prevent accidental slipping of the slider 3300. In some embodiments, a slider 3300 design which eliminates force along the axis of movement when a user pulls from the leg. Internal cut 3130 and its features may provide slider 3300 position retention when a user is not applying force to the slider 3300 itself.

FIGS. 32A, 32B, and 32C depict a housing 3200 which includes a cut 3210, and holes 3220, according to some embodiments. In some embodiments, the cut 3210 is sized to fit leg 3400, allowing leg 3400 rotation about a pin aligned with center axis of holes 3220. As slider 3300 position is adjusted, leg 3400 rotation occurs, opening the pen for EEG acquisition.

Figure 33A:
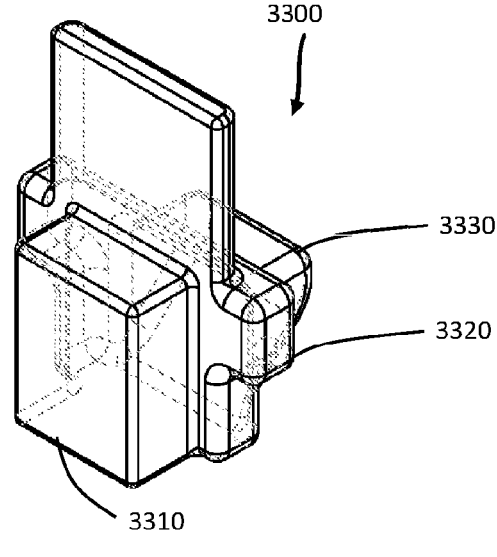
FIG. 33A illustrates an isometric view of slider showing external, internal and side extrusions used to locate the slider between body and housing, according to some embodiments.
Figure 33B:
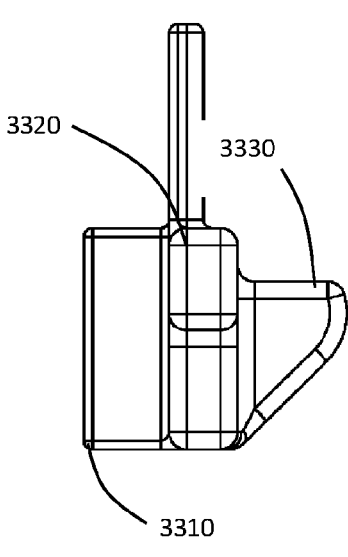
FIG. 33B illustrates a side view of slider showing external, internal and side extrusions used to locate the slider between body and housing, according to some embodiments.

FIGS. 33A and 33B illustrate slider 3300 with external extrusion 3310, side extrusion 3320, and internal extrusion 3330, according to some embodiments. In some embodiments, external extrusion 3310 serves as a touch point for the user when moving the slider 3300 to open the leg 3400. Side extrusion 3320 interfaces with internal cut 3130 of body 3100 to maintain the slider 3300 in contact with leg 3400. In some embodiments, internal extrusion 3330 interfaces with external cut 3410 of leg 3400 to open or close the leg 3400 when an external force is applied to slider 3300.

FIG. 34 illustrates leg 3400 including cut 3410 and holes 3420. Cut 3410 is sized to fit internal extrusion 3330 of slider 3300, according to some embodiments. As the slider 3300 moves, internal extrusion 3330 will translate applied force on slider 3300 into force on cut 3410 of leg 3400 to rotate leg 3400 about hole 3420 which sits on axis with hole 3220 of housing 3200.

Figure 35A:
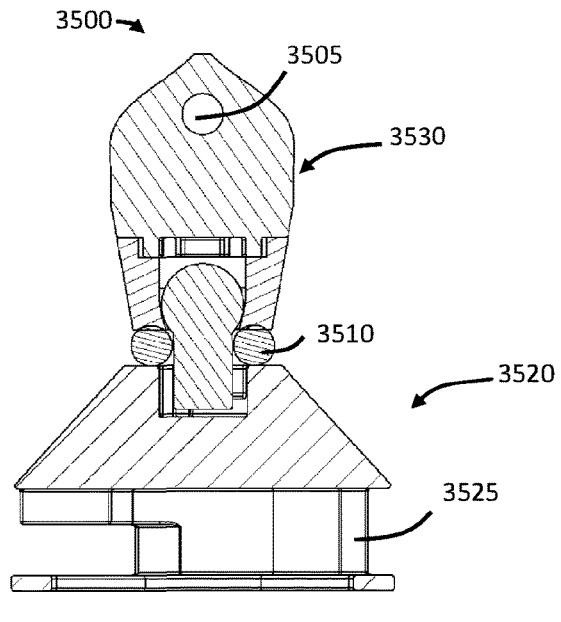
FIGS. 35A and 35B depict a foot component of the biosignal acquisition device, according to some embodiments.
Figure 35B:
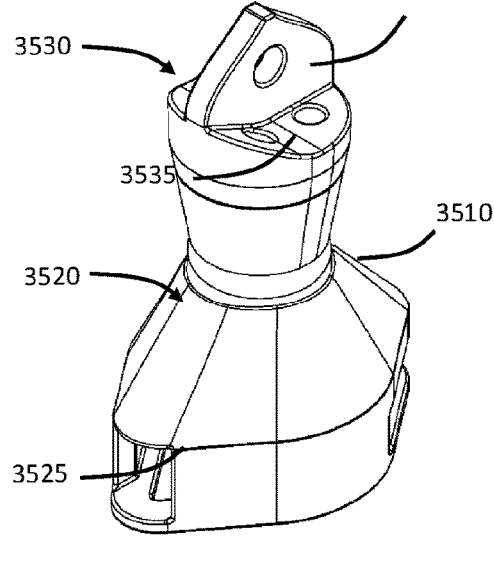

FIGS. 35A and 35B depict a foot 3500 comprising compressible pad 3510 to reduce motion artifacts during use, according to some embodiments. In some embodiments, the compressible pad 3510 is provided between a top section 3530 and a bottom section 3520 of the foot 3500. In some embodiments, an electrode is received by a cut 3525 of bottom section 3520 of the foot 3500. In some embodiments, a tension wire or tendon attaches through cuts 3535 on top section 3530. In some embodiments, the foot 3500 connects to leg through a pin fixed in hole 3505.

Figure 37:
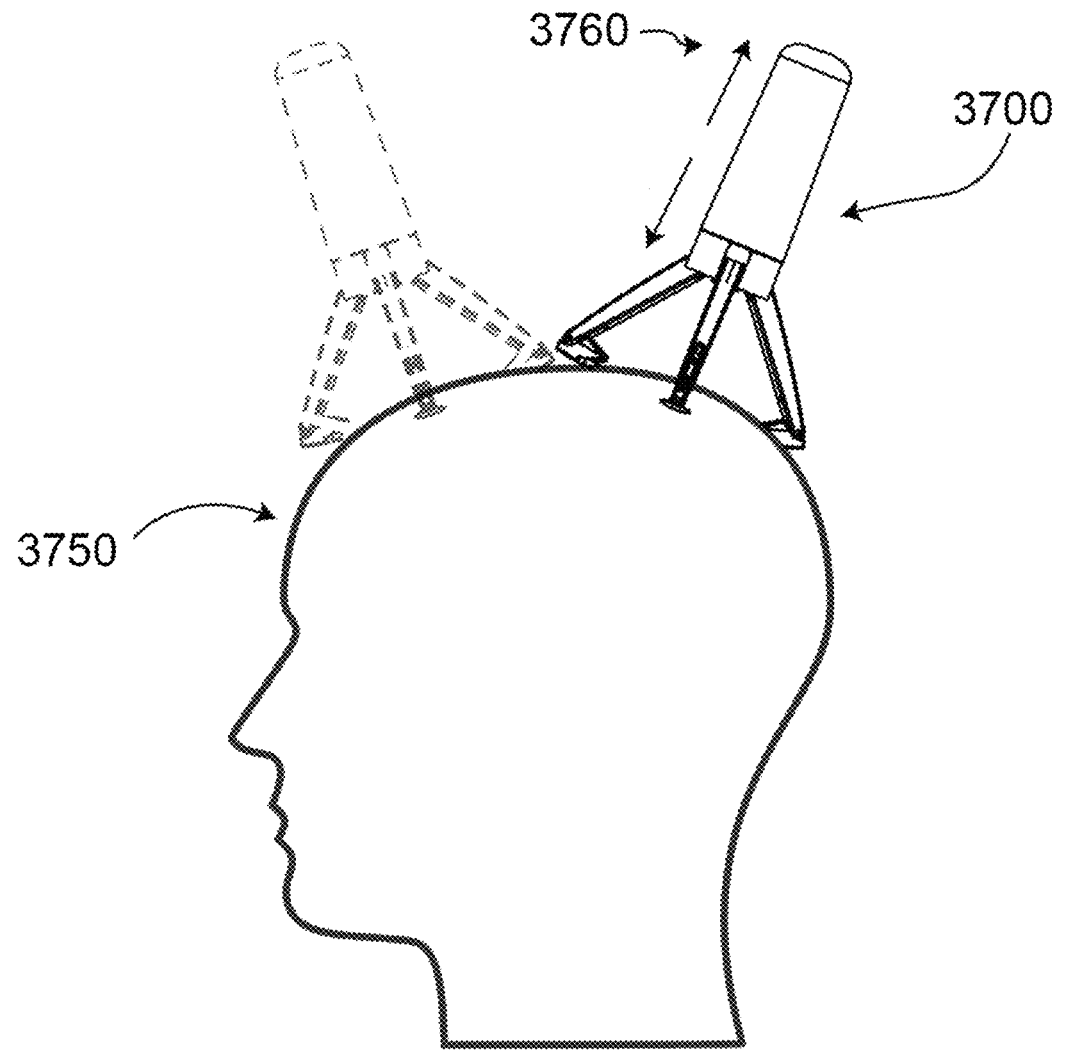
FIG. 37 depicts placement of a portable biosignal acquisition device on a scalp of a subject, according to some embodiments.

FIG. 37 depicts a device 3700 that can be positioned on the scalp 3750 of the subject for bioelectric signal acquisition or stimulation is provided, according to some embodiments. In some embodiments, the device is temporarily placed on the subject scalp 3750 by a downward user-applied force 3760 to achieve sufficient contact between the electrodes and the scalp. Similarly, the devices may be withdrawn from a configuration on the scalp 3750 by the removal of the applied force for repositioning on another configuration. In some embodiments, the downward user-applied force 3760 on the electrode for connection with the subject's scalp 3750 may be further improved by the application of conductive gel.

In some embodiments, a pEEG hardware has dimensions of 31×140 (mm) in a closed state and 95×120 (mm) in an open state. In some embodiments, the device comprises pivoting legs. In some embodiments, the legs are about 57.2 mm long. In some embodiments, an electrode-applying foot is provided at a distal end of each leg. In some embodiments, the foot is connected to the pivoting leg by a pin joint. In some embodiments, the pin joint is a 2 mm pin joint. In some embodiments, the foot holds a 10 mm diameter gold-cup electrode and is controlled by a 120 mm tension-wire. The tension-wire or tendon is routed from the electrode-applying foot through the pivoting leg and secures to the housing. The tension-wire effective length may vary as the pivoting leg is opened or closed. As the length varies, the electrode-applying foot angle may be adjusted accordingly, providing increased flexion when the leg is in an open position. The tendon or tension-wire control method paired with rubber dampeners at the feet may absorb subtle movements of the operator's hand due to related and emergent factors that may occur while the pEEG is in use. Use of an elastic tendon or tension-wire control and rubber dampeners above the electrodes may passively reduce motion artifacts while providing conformance to the patient's head shape and size.

In some embodiments, the body or housing comprises medical-grade polycarbonate. In some embodiments, pEEG comprises an additional port for a 40-cm wire-based conductive adhesive electrode that may be neck-mounted to provide an active ground. In some embodiments, use of an additional conductive electrode increases the effective Common Mode Rejection Ration (CMRR) by approximately 20 dB.

In some embodiments, the device further comprises one or more force sensors to sense the force applied at the electrodes. In some embodiments, the force sensors are 7×7 mm. In some embodiments, the force sensors are analog force sensors. In some embodiments, the device comprises three force sensors. In some embodiments, the force sensors are enclosed in the pEEG housing to sense the force applied at each electrode for use in the smart feedback system.

The guided electrode positioning system (GePS) may provide positioning data corresponding to the position of the electrodes through image-based feature tracking which integrates inertial data from an accelerometer and gyroscope enclosed in the central housing. In some embodiments, the GePS further utilizes visual input from one or more cameras (e.g. 1610 as depicted in FIG. 16). In some embodiments, the camera comprises a 120° field of view (FOV).

In some embodiments, a camera for GePS will be recessed into the housing at an offset from the central line with respect to the reference electrode. In some embodiments, the offset is about 12 mm. In some embodiments, the offset avoids increasing the housing size while keeping the electrodes in the 120° field of view for tracking. In some embodiments, the force sensor diaphragm located in the housing will transduce responses from a dynamic lever mechanism attached to the pivoting leg joint to relay the force experienced by the electrode-applying foot as the pEEG is positioned on the scalp.

Transmission will be facilitated by a low-power, multi-protocol 2.4 GHz Bluetooth wireless microcontroller (MCU). The device may be powered by a lithium-polymer battery. The battery may be supported by a battery manager. A charging port (e.g. 430 depicted in FIGS. 4A and 4B) may be provided to recharge the battery.

In some embodiments, the device pairs with a custom cross-platform application (IOS, Android and Windows) deployed on a Bluetooth-capable or Wi-Fi capable mobile device, to display the EEG signals. Data may be stored on the hospital's servers and accessible through a web application. Integration of mechanical design, smart electronics and GePS constitutes the pEEG ecosystem that is designed to offer seamless user-application. In some embodiments, the device is part of a smart feedback system, which measures electrode-scalp impedance and applied electrode contact force, then calculates and displays a color-coded electrode quality metric to the operator.

The utilization of the tendon or tension-wire in combination with the compressible pads on which the electrodes are disposed, according to some embodiments, is essential in maintaining sufficient contact with the skin surface to obtain accurate readings from the electrodes. In some embodiments, the tendons or tension wires bias the legs and electrodes provided thereon towards a center axis of the portable device. This system facilitates measurement of the of electrical signals with the electrodes, such that testing using the portable device may be self-administered or administered by a user who has little or no training in placement of electrodes and subsequent measurement of electrical signals. Ease of use may be especially important when obtaining sensitive measurements, such as recording electrical activity of the brain obtained by placing the electrodes on a scalp of a subject to generate an electroencephalogram. In some embodiments, systems, such as a smart feedback system described herein, further facilitate proper electrode contact is provided against the skin surface.

Figure 36:
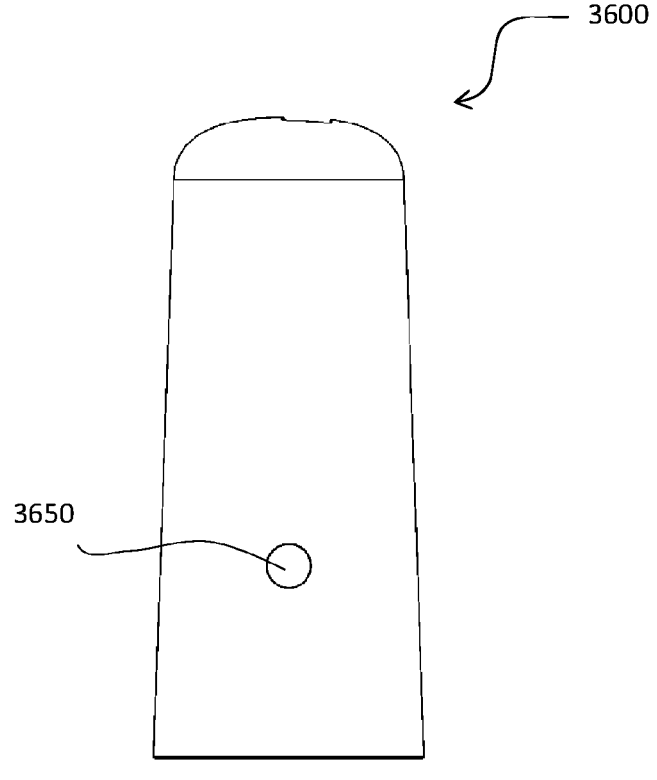
FIG. 36 depicts a housing of the biosignal acquisition device, according to some embodiments.

In some embodiments for clinical-grade signal-to-noise ratio (SNR), the electronics may be tuned to provide 1) common-mode input impedance (>100 MΩ at 60 Hz), 2) differential mode input-impedance (>10 MΩ at 60 Hz) and 3) high common mode rejection ratio (>80 dB at 60 Hz). The analog-digital circuit may be designed on a printed circuit board (PCB). The PCB may be a 15×40 (mm) six-layer PCB. The analog signal may be transduced by an analog front-end CMOS chip and digitized with a 24-bit analog-to-digital converter for biopotential measurements. A detachable electrode connected through the additional port may act as a bias drive increasing the effective CMRR while decreasing the ambient 60 Hz common mode noise that may appear due to electrode impedance mismatches. FIG. 36 depicts a housing 3600 comprising an additional port 3650 for receiving a detachable electrode, according to some embodiments. Integration of the bias drive may provide electrical isolation by dynamically driving up to 0.01 mV into the patient based on the interfering common voltage. The bias drive addition may reduce the interference observed due to the capacitive coupling of 60 Hz mains voltage and electrical equipment present inside the hospital rooms. Gold-cup electrodes may be attached to a shielded wire and positioned within the electrode legs to reduce the effects of electromagnetic interference on the EEG signal. The PCB may be encased in aluminum shielding to further minimize radiative interference. The ADC on the analog chip may be programmed for signal acquisition at 256 Hz sampling frequency. The information from the force sensors may be sampled at 2 Hz. Electrode impedance mismatches may be within 1-2 kΩ to minimize signal degradation.

The GePS may utilize image and inertial signal processing to provide the operator with simple visual cues. The cues may reflect the electrode's actual position (AP) and the indicated position (IP) on a 10-20 EEG configuration figure on the tablet. AP may be calculated with respect to the electrode's IP which are the specific locations suggested in the NCSE-specific GePS approach. A dedicated section on the tablet recording screen may display targeted electrode placement adjustments to the operator as a message prompt. Electrode placement success may be indicated to the operators as a green highlight when AP and IP coincide for the specific configuration. Calculations which may locate each electrode's placement are performed by the tablet's software interface or in the pEEG embodiment. In some embodiments, the recorded images are not visible to the operator. Images (in RGB) from the ultraminiaturized camera may be acquired at 30 frames per second (fps) with 640×480 pixels resolution. An initial set of images to mark an origin may be captured at least 5 mm above the center of the patient scalp. The 120° field of view along with the selected leg length (~57 mm in some embodiments) may capture electrode positions with respect to the subject's scalp across the fronto-polar, frontal, central and parietal regions. Separate images may be recorded for temporal and occipital locations. The intensities of the 2D RGB array for each image may be readjusted to extract the contours of the scalp. The fps may be dynamically adjusted to minimize computational load by recording at a lower fps rate (e.g. 5 fps) when the force sensors report that the electrodes are placed on the scalp and a higher fps rate (e.g. 30 fps) when the electrodes lift-off. GePS performance may be finetuned to ensure AP is within 15 mm radius of IP.

Clinical research reveals that the predominant NCSE locations are in the frontal lobe followed by the temporal lobes. Specific electrode configurations from these predominant regions form the pEEG screening approach and may be displayed as visual cues (indicated positions or IP) on the tablet. At each configuration on the tablet, the operator may record thirty-second epochs to quantify the EEG patterns using feature classification algorithm. In practice, the operator may be directed by the tablet to place the 2-channel pEEG at a bihemispheric frontal lobe configuration (e.g. F3-F4-Cz) to detect any bilateral activity, indicating a generalized seizure episode. If bilateral activity is observed at the first location, the NCSE-specific approach may direct the operator to monitor two additional configurations symmetrical to the midsagittal plane (e.g. Fp1-Fp2-Cz and P3-P4-Cz). If only unilateral activity is observed at the first location, two subsequent hemisphere-specific configurations (e.g. left: F3-P3-Cz followed by T3-T5-M1 or right: F4-P4-Cz followed by T4-T6-M2) may be displayed to the operator for localizing the source of abnormal activity. In some embodiments, the feature classification performance will not be hampered considering the electrodes are within a 15 mm radius from the suggested IP.

In some embodiments, EEG signals will undergo time-frequency (TF) decomposition using discrete wavelet transform (DWT). The decomposition may segment the EEG into sub-bands using fourth order Daubechies wavelets to calculate approximate (A1-4) and detail (D1-4) coefficients for each sub-band. In some embodiments, the sub-band frequency ranges are: D1 (64-128 Hz), D2 (32-64 Hz), D3 (16-32 Hz), D4 (8-16 Hz) and A4 (0-8 Hz). Extracted statistical parameters such as variance, standard deviation, and amplitude from the decomposed signals will be input to a naive Bayes (NB) classifier for feature classification. The NB classifier is based on the Bayesian theory that requires a minimal number of training datasets and has a high seizure feature classification accuracy of up to 98.65%.

When following the NCSE-specific approach, there may be expected scalp locations that are not easily reached by the electrode. In this situation, actions may be taken to allow for access to these scalp locations: 1) the tension-wire may be lengthened so the foot may reach a more acute electrode angle to accommodate perpendicular scalp surfaces, 2) different pivoting leg lengths may be printed and prepared to accommodate diverse head sizes, 3) improved pEEG housing mechanisms may be implemented to accommodate for limitations not addressed by adjusting tension-wire or leg length. In some embodiments, the device may implement an additional "knee" joint to improve pEEG dexterity and electrode contact.

I. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The terms "subject," "individual," or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

As used herein, the term "about" a number refers to that number plus or minus 10% of that number. The term "about" a range refers to that range minus 10% of its lowest value and plus 10% of its greatest value.

The section headings used herein are for organizational purposes only and are not to be construed as limiting the subject matter described.

II. EXAMPLES

The following examples are included for illustrative purposes only and are not intended to limit the scope of the invention.

Example 1: Evaluation of a Single-Channel pEEG

In some embodiments, a single-channel pEEG functional device with essential hardware and software features has undergone testing that included: 1) evaluation of mechanism function for electrode-skin contact consistency and 2) circuit performance while acquiring posterior dominant rhythms from healthy adult subjects. Mechanical enclosure had a physical limiter to restrict the pivoting leg opening to 45° with respect to the central pen axis (as depicted in FIG. 1B). An inter-electrode separation of 52.8 mm was allowed for reliable recordings while minimizing magnetic induction interference. The center of mass was closer to the base of the housing where the operator held the device, providing balance for short-term recordings. The enclosure was produced with Formlabs 3 stereolithography 3D printers. Circuit utilized a two-stage analog bandpass filter (1-34 Hz) and a microcontroller on a custom 15×45 (mm) six-layer PCB. An ultra-low noise instrumentation amplifier with a low 200 pA bias current and 100 dB CMRR was selected to maximize signal quality. The analog signals were sampled at 256 Hz. Data processing and signal acquisition was performed on a custom-designed iOS application. The application paired with the pEEG hardware via Bluetooth and displayed EEG signals on an iPad Pro 11-inch screen. Flexible real-time infinite impulse response (IIR) digital filters with low and high frequency cut-off were added to provide tunable filtering options. A real-time fast-Fourier transform (FFT) chart displayed power in the frequency domain to monitor signal noise level. Posterior dominant rhythm study was conducted on three untrained subjects who were directed to open and close their eyes via audio cues at 20-second intervals. The pEEG electrodes were applied at O2 for recording, T4 as ground and M2 as reference. Scalp locations were exfoliated with Nuprep cream and the gold-cup electrodes were applied using 10-20 conductive gel. The operator was able to hold the handheld pEEG for 4 minutes without discomfort. Anonymized data for 150 trials was post-processed in MATLAB to calculate alpha band power values between eye open and close events. Outcomes: Posterior dominant rhythms alpha power increase when the subjects closed their eyes, which is consistent with the existing EEG systems. The increase in power was verified by a one-sign tail test which reported statistical significance ($p<0.001$).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A handheld device for receiving electric signals from a surface to detect electrical activity comprising:

a housing including a distal end and a proximal end;

a battery;

at least a plurality of legs extending from the proximal end of the housing, each leg of the plurality of legs includes a foot provided at a distal end of the leg; and one or more electrodes provided on each foot associated with a leg of the plurality of legs, wherein each of the one or more electrodes is configured to detect electroencephalogram electrical signals when the one or more electrodes is placed on the head of the patient, wherein the handheld device is constructed to allow, during operation, movement of the handheld device to different locations on the head to detect the electroencephalogram electrical signals representative of brain activity of the patient.

2. The handheld device of claim 1, further comprising one or more sensors configured to determine a position of the one or more electrodes.

3. The handheld device of claim 2, further comprising a first computing device provided within the housing, the first computing device comprising a processor operatively coupled to the one or more sensor and a non-transitory computer readable storage medium with a computer program including instructions executable by the processor causing the processor to: i) calibrate a position of the one or more electrodes and set an origin, ii) receive data from the one or more sensors to track the position of the one or more electrodes, and iii) record the electric signals detected by the one or more electrodes.

4. The handheld device of claim 3, wherein the processor of the first computing device is further configured to transmit the electrical signals to a second computing device, the second computing device configured to receive the electric signals transmitted from the first computing device of the portable device and positional data corresponding to the position of the one or more electrodes, and wherein the second computing device comprises a second processor and a non-transitory computer readable storage medium with a second computer program including instructions executable by the processor causing the second processor to generate a graphical representation of the electrical signals detected by the one or more electrodes.

5. The handheld device of claim 4, wherein the second computer program further comprises instructions to generate a graphical representation of the positional data of the one or more electrodes.

6. The handheld device of claim 5, wherein the first computing device communicates to the second computing device via wireless networking including a short range wireless technology, an ultrawide-band or a Wireless Fidelity (Wi-Fi) transmission.

7. The handheld device of claim 2, wherein the one or more sensors include at least (i) an image sensor operating as a camera such that the one or more electrodes are within a field of view of the camera.

8. The handheld device of claim 3, wherein the one or more sensors include one or more inertial sensors, and wherein the computer program includes further instructions causing the processor to receive data from the one or more inertial sensors to track the position of the one or more electrodes.

9. The handheld device of claim 8, wherein the one or more inertial sensors provide a six-axis measurement.

10. The handheld device of claim 1, wherein the housing further comprises a port for reversibly receiving a wire electrode.

11. The handheld device of claim 1, wherein each foot associated with a leg of the plurality of legs comprises a compressible pad.

12. The handheld device of claim 1, wherein each leg of the plurality of legs is connected to a corresponding foot via a pin joint.

13. The handheld device of claim 2, wherein the one or more sensors include one or more force sensors, wherein each force sensor of the one or more force sensors, provided to a corresponding leg of the plurality of legs, measures a force applied to the surface by an electrode of the one or more electrodes applied to an end of the corresponding leg.

14. The handheld device of claim 13, wherein one force sensor is provided for each of the plurality of legs.

15. The handheld device of claim 1, wherein the housing is an elongated housing portable device further comprises one or more force sensors, wherein the force sensors measure a force applied to the surface of the subject by the one or more electrodes.

16. The handheld device of claim 15 further comprising:

one or more force sensors, wherein the force sensors measure a force applied to the surface of the subject by the one or more electrodes and the one or more electrodes comprise cup electrodes.

17. The handheld device of claim 15, wherein the housing further comprises a port for reversibly receiving a wire electrode.

18. The handheld device of claim 1, wherein the portable device comprises a closed configuration and an open configuration, wherein the one or more electrodes are closer to one another in the closed configuration than in the open configuration.

19. The handheld device of claim 18 further comprising one or more tension wires configured to bias the plurality of legs to the closed configuration in lieu of the open configuration.

20. The handheld device of claim 19, wherein the housing comprises openings sized to fit the plurality of legs to limit a distance between the one or more electrodes in the open configuration.

21. The handheld device of claim 1, wherein the housing comprises openings sized to fit the plurality of legs to limit a distance between the one or more electrodes.

22. The handheld device of claim 1, wherein the plurality of legs extending from the proximal end of the housing comprises three legs.

23. The handheld device of claim 1 further comprising an actuator to rotate the plurality of legs toward or away from a center axis of the handheld device so that the one or more electrodes at the distal ends of the plurality of legs move toward or away from one another.

24. The handheld device of claim 23, wherein rotation of the plurality of legs comprises a rotation toward or away from a center axis of the housing such that each of the one or more electrodes moves toward or away from one another.

25. The handheld device of claim 24, wherein the actuator rotates the plurality of legs simultaneously.

26. The handheld device of claim 25, wherein one or more tension wires are configured to keep the one or more electrodes in contact with the surface.

27. The handheld device of claim 1, wherein the head of the patient is a skin surface of the patient or a scalp of the patient.

28. The handheld device of claim 1, wherein the plurality of legs extending angularly from the proximal end of the housing and each leg of the plurality of legs is pivotally attached to the foot.

29. A method for detecting electric signals with a handheld device operating as at least an electroencephalogram device that comprises a housing, one or more legs extending from the housing, and one or more electrodes provided on a distal end of each of the one or more legs, the method comprising:

a. placing, with user applied force, the one or more electrodes on a head surface of a subject to detect one or more electroencephalogram electric signals from a first region of the head surface of the subject;

b. after detecting the one or more electroencephalogram electric signals at the first region of the head surface of the subject, moving the one or more electrodes to one or more subsequent regions of the head surface of the subject; and c. detecting one or more electroencephalogram electric signals from the one or more subsequent regions of the head surface of the subject until electroencephalogram electrical signals inclusive of the one or more electroencephalogram electric signals have been obtained from all desired regions of the head surface of the subject including at least the first region and the one or more subsequent regions.

30. The method of claim 29, wherein the moving of the one or more electrodes to the one or more subsequent regions of the head surface of the subject further comprises keeping the one or more electrodes in contact with the head surface of the subject.

31. The method of claim 29, further comprising holding the one or more electrodes at the first region and holding the one or more electrodes at the one or more subsequent regions.

32. The method of claim 31, further comprising receiving feedback from the handheld device prior to moving the one or more electrodes to the one or more subsequent regions.

33. The method of claim 32, wherein the feedback is indicative of the transmitting of the electrical signals obtained by the one or more electrodes.

34. The method of claim 32, wherein the feedback is indicative of the capturing and storing of data corresponding to the electrical signals obtained by the one or more electrodes.

35. The method of claim 34, wherein the data comprises a position of each of the one or more electrodes.

36. The method of claim 34, wherein the data comprises voltage fluctuations detected by the one or more electrodes.

37. The method of claim 32, wherein the feedback comprises haptic feedback, visual feedback, or a combination thereof.

38. The method of claim 29, wherein the head surface of the subject is a scalp.

39. The method of claim 38 further comprising generating an electroencephalogram based on the detected one or more electric signals.

40. The method of claim 29, further comprising:

engaging a button on the handheld device to calibrate the position of the one or more electrodes at the origin.

41. A method for detecting electric signals with a handheld device operating as at least an electroencephalogram device that comprises a housing, one or more legs extending from the housing, and one or more electrodes provided on a distal end of each of the one or more legs, the method comprising:

placing the one or more electrodes on a surface of a subject to detect one or more electroencephalogram electric signals from a first region of the surface of the subject;

moving the one or more electrodes to one or more subsequent regions of the surface of the subject upon detecting the one or more electroencephalogram electric signals from the first region;

detecting one or more electroencephalogram electric signals from the one or more subsequent regions of the surface of the subject; and repeating the moving and detecting operations until electroencephalogram electric signals have been obtained from all desired regions of the surface of the subject including at least the first region and the one or more subsequent regions, wherein the handheld device further comprises one or more sensors configured to determine a position of the one or more electrodes; and a computing device provided within the housing, the computing device comprises a processor operatively coupled to the image sensor and a non-transitory computer readable storage medium with a computer program including instructions executable by the processor causing the processor to: i) calibrate a position of the one or more electrodes and set an origin, ii) receive data from the one or more sensors to track the position of the one or more electrodes, and iii) record electric signals obtained from the one or more electrodes.

42. The method of claim 41, wherein the processor of the computing device is further configured to transmit the electroencephalogram electrical signals to an external computing device.

\* \* \* \* \*